(12) United States Patent
Payne et al.

(10) Patent No.: US 10,603,388 B2
(45) Date of Patent: Mar. 31, 2020

(54) METHODS FOR FORMULATING ANTIBODY DRUG CONJUGATE COMPOSITIONS

(71) Applicant: ImmunoGen, Inc., Waltham, MA (US)

(72) Inventors: Gillian Payne, Waban, MA (US); Robert W. Herbst, Braintree, MA (US); Juma Bridgewater, Tolland, CT (US)

(73) Assignee: ImmunoGen, Inc., Waltham, MA (US)

( * ) Notice: Subject to any disclaimer, the term of this patent is extended or adjusted under 35 U.S.C. 154(b) by 232 days.

(21) Appl. No.: 15/678,505

(22) Filed: Aug. 16, 2017

(65) Prior Publication Data

US 2017/0348428 A1 Dec. 7, 2017

Related U.S. Application Data

(62) Division of application No. 14/843,769, filed on Sep. 2, 2015, now abandoned.

(60) Provisional application No. 62/044,592, filed on Sep. 2, 2014.

(51) Int. Cl.
| | |
|---|---|
| *A61K 47/68* | (2017.01) |
| *C07K 16/28* | (2006.01) |
| *C07K 16/30* | (2006.01) |
| *A61K 39/00* | (2006.01) |

(52) U.S. Cl.
CPC ...... *A61K 47/6803* (2017.08); *A61K 47/6849* (2017.08); *A61K 47/6851* (2017.08); *C07K 16/28* (2013.01); *C07K 16/2803* (2013.01); *C07K 16/2863* (2013.01); *C07K 16/30* (2013.01); *A61K 2039/505* (2013.01); *A61K 2039/545* (2013.01); *C07K 2317/24* (2013.01); *C07K 2317/73* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,256,746 A | 3/1981 | Miyashita et al. | |
| 4,294,757 A | 10/1981 | Asai | |
| 4,307,016 A | 12/1981 | Asai et al. | |
| 4,313,946 A | 2/1982 | Powell et al. | |
| 4,315,929 A | 2/1982 | Freedman et al. | |
| 4,322,348 A | 3/1982 | Asai et al. | |
| 4,331,598 A | 5/1982 | Hasegawa et al. | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,424,219 A | 1/1984 | Hashimoto et al. | |
| 4,444,887 A | 4/1984 | Hoffmann | |
| 4,450,234 A | 5/1984 | Hasegawa et al. | |
| 4,563,304 A | 1/1986 | Carlsson et al. | |
| 4,716,111 A | 12/1987 | Osband et al. | |
| 5,208,020 A | 5/1993 | Chari et al. | |
| 5,225,539 A | 7/1993 | Winter | |
| 5,416,064 A | 5/1995 | Chari et al. | |
| 5,475,092 A | 12/1995 | Chari et al. | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,585,089 A | 12/1996 | Queen et al. | |
| 5,585,499 A | 12/1996 | Chari et al. | |
| 5,639,641 A | 6/1997 | Pedersen et al. | |
| 5,814,318 A | 9/1998 | Lonberg et al. | |
| 5,846,545 A | 12/1998 | Chari et al. | |
| 6,333,410 B1 | 12/2001 | Chari et al. | |
| 6,441,163 B1 | 8/2002 | Chari et al. | |
| 6,716,821 B2 | 4/2004 | Zhao et al. | |
| 7,276,497 B2 | 10/2007 | Chari et al. | |
| 7,342,110 B2 | 3/2008 | Hoffee et al. | |
| 7,368,565 B2 | 5/2008 | Chari et al. | |
| 7,473,796 B2 | 1/2009 | Chari et al. | |
| 7,557,189 B2 | 7/2009 | Hoffee et al. | |
| 7,662,361 B2 | 2/2010 | Au et al. | |
| 7,834,155 B2 | 11/2010 | Payne et al. | |
| 7,989,598 B2 | 8/2011 | Steeves et al. | |
| 8,119,787 B2 | 2/2012 | Hoffee et al. | |
| 8,163,888 B2 | 4/2012 | Steeves et al. | |
| 8,198,417 B2 | 6/2012 | Steeves et al. | |
| 8,236,319 B2 | 8/2012 | Chari et al. | |
| 8,337,855 B2 | 12/2012 | Hoffee et al. | |
| 8,435,528 B2 | 5/2013 | Chari et al. | |
| 8,557,966 B2 | 10/2013 | Ab et al. | |

(Continued)

FOREIGN PATENT DOCUMENTS

| | | |
|---|---|---|
| EP | 0519596 A1 | 12/1992 |
| EP | 0239400 B1 | 8/1994 |

(Continued)

OTHER PUBLICATIONS

Search Report and Written Opinion for Singaporean Patent Application No. 11201701328X, Intellectual Property Office of Singapore, Singapore, dated Apr. 10, 2108, 10 pages.

Extended European Search Report and European Search Opinion for EP Application No. EP 15837813, The Hague, Netherlands, dated Mar. 20, 2018, 11 pages.

Ab et al., "Abstract 4576: IMGN853, an anti-Folate Receptor I antibody-maytansinoid conjugate for targeted cancer therapy," Cancer Res, p. 71 (8 Suppl), United States (2011).

Al-Lazikani, B., et al., "Standard Conformations for the Canonical Structures of Immunoglobulins," Journal of Molecular Biology 273(4):927-948, Academic Press Limited, United States (Nov. 1997).

(Continued)

*Primary Examiner* — Brad Duffy

(74) *Attorney, Agent, or Firm* — Sterne, Kessler, Goldstein & Fox P.L.L.C.

(57) ABSTRACT

The present invention provides improved methods for formulating therapeutic compositions comprising an antibody drug conjugate ("ADC") that reduce potency variability between batches of ADC and provide for administration of such therapeutic compositions within a narrow intended range.

7 Claims, 15 Drawing Sheets

Specification includes a Sequence Listing.

(56) References Cited

U.S. PATENT DOCUMENTS

| | | |
|---|---|---|
| 8,563,509 B2 | 10/2013 | Steeves et al. |
| 8,709,432 B2 | 4/2014 | Carrigan et al. |
| 8,765,740 B2 | 7/2014 | Li et al. |
| 8,765,917 B2 | 7/2014 | Deckert et al. |
| 8,790,649 B2 | 7/2014 | Setiady et al. |
| 9,289,509 B2 | 3/2016 | Osterroth et al. |
| 2005/0065086 A1 | 3/2005 | Kirk et al. |
| 2006/0177455 A1 | 8/2006 | Hoffee et al. |
| 2008/0315821 A1 | 12/2008 | Chen |
| 2009/0202536 A1 | 8/2009 | Ebens, Jr. et al. |
| 2009/0274713 A1 | 11/2009 | Chari et al. |
| 2011/0123554 A1 | 5/2011 | Osterroth et al. |
| 2012/0009181 A1 | 1/2012 | Ab et al. |
| 2012/0244171 A1 | 9/2012 | Li et al. |
| 2012/0282282 A1 | 11/2012 | Lutz et al. |
| 2013/0029900 A1 | 1/2013 | Widdison |
| 2013/0156796 A1 | 6/2013 | Setiady et al. |
| 2013/0302359 A1 | 11/2013 | Li et al. |
| 2016/0058884 A1 | 3/2016 | Payne et al. |

FOREIGN PATENT DOCUMENTS

| | | |
|---|---|---|
| EP | 0592106 B1 | 11/2004 |
| EP | 2550975 A1 | 1/2013 |
| EP | 2694105 A2 | 2/2014 |
| WO | WO-9109967 A1 | 7/1991 |
| WO | WO-9110741 A1 | 7/1991 |
| WO | WO-9633735 A1 | 10/1996 |
| WO | WO-9634096 A1 | 10/1996 |
| WO | WO-9816654 A1 | 4/1998 |
| WO | WO-9824893 A2 | 6/1998 |
| WO | WO-9846645 A2 | 10/1998 |
| WO | WO-9850433 A2 | 11/1998 |
| WO | WO-2004103272 A2 | 12/2004 |
| WO | WO-2005009369 A2 | 2/2005 |
| WO | WO 2006/062779 A2 | 6/2006 |
| WO | WO-200702422 A1 | 3/2007 |
| WO | WO-2008119353 A1 | 10/2008 |
| WO | WO-2009134976 A1 | 11/2009 |
| WO | WO-2009134977 A1 | 11/2009 |
| WO | WO 2011/039724 A1 | 4/2011 |
| WO | WO-2011106528 A1 | 9/2011 |
| WO | WO-2011112978 A1 | 9/2011 |
| WO | WO-2011131746 A2 | 10/2011 |
| WO | WO-2012058588 A2 | 5/2012 |
| WO | WO 2012/112687 A1 | 8/2012 |
| WO | WO 2012/135740 A2 | 10/2012 |
| WO | WO-2012177837 A2 | 12/2012 |
| WO | WO 2013/043933 A2 | 3/2013 |
| WO | WO 2016/036801 A1 | 3/2013 |
| WO | WO 2016/036804 A1 | 3/2013 |
| WO | WO 2014/055877 A1 | 4/2014 |
| WO | WO 2015/014879 A1 | 2/2015 |
| WO | WO 2016/035794 A1 | 3/2016 |

OTHER PUBLICATIONS

Carlsson, J., et al., "Protein Thiolation and Reversible Protein-protein Conjugation. N-succinimidyl 3-(2-pyridyldithio)propionate, a New Heterobifunctional Reagent," The Biochemical Journal 173(3):723-737, Portland Press on behalf of the Biochemical Society, England (1978).

Desnoyers, L.R., et al., "Tumor-Specific Activation of an EGFR-Targeting Probody Enhances Therapeutic Index," Science Translational Medicine 5(207):207ra144 United States (Oct. 2013).

Green, B. and Duffull, S.B., "What is the Best Size Descriptor to Use for Pharmacokinetic Studies in the Obese?," British Journal of Clinical Pharmacology 58(2):119-133, Blackwell Publishing Ltd., England (2004).

Herbst, R.W., IBC Bioconjugates talk: Advancing a New Payload for Antibody Drug Conjugates Through Early Phase Development: Lessons from Process and Analytical Development (May 2015).

Hu, S., et al., "Minibody: A Novel Engineered Anti-carcinoembryonic Antigen Antibody Fragment (Single-Chain Fv-CH3) which Exhibits Rapid, High-level Targeting of Xenografts," Cancer Research 56(13):3055-3061, American Association for Cancer Research, United States (Jul. 1996).

International Search Report and the Written Opinion for International Application No. PCT/US2015/048152, the International Searching Authority, dated Dec. 28, 2015, 12 pages.

Jones, P.T., et al., "Replacing the Complementarity-determining Regions in a Human Antibody with those from a Mouse," Nature 321(6069):522-525, Nature Publishing Group, England (May 1986).

Kennett, S., IABS_Setting Specification: Regulatory Expectations for Setting Specifications at Early Stages of Development, United States (Sep. 2013).

Miller et al., "Abstract 652: Antibody-Drug Conjugates(ADCs) of Indolino-Benzodiazepine DNA-Alkylating Agents," Cancer Research 2015:75 United States (Apr. 2015).

Padlan, E.A., "A Possible Procedure for Reducing the Immunogenicity of Antibody Variable Domains While Preserving their Ligand-binding Properties," Molecular Immunology 28(4-5):489-498, Pergamon Press, England (Apr. 1991).

Riechmann, L., et al., "Reshaping Human Antibodies for Therapy," Nature 332(6162):323-327, Nature Publishing Group, United States (Mar. 1988).

Roguska, M.A., et al., "Humanization of Murine Monoclonal Antibodies through Variable Domain Resurfacing," Proceedings of the National Academy of Sciences USA 91(3):969-973, National Academy of Sciences, United States (Feb. 1994).

Studnicka, G.M., et al., "Human-Engineered Monoclonal Antibodies Retain Full Specific Binding Activity by Preserving Non-CDR Complementarity-Modulating Residues," Protein Engineering 7(6):805-814, Oxford University Press, England (1994).

Verhoeyen, M., et al., "Reshaping Human Antibodies: Grafting an Antilysozyme Activity," Science 239(4847):1534-1536, American Association for the Advancement of Science, United States (Mar. 1988).

Office Action dated Jan. 9, 2019, in U.S. Appl. No. 14/843,769, Payne, G. et al., filed Sep. 2, 2015, 12 pages.

Galush W.J., et al., "Formulation development of antibody-drug conjugates," Methods Mol Biol 1045: 217-33, Humana Press, United States (2013).

Hamblett, K., et al., "Effects of drug loading on the antitumor activity of a monoclonal antibody drug conjugate," Clin Cancer Res 10(20):7063-70, The American Association for Cancer Research, United States (2004).

Panowski, S., et al., "Site-specific antibody drug conjugates for cancer therapy," MABS 6(1): 34-45, Taylor & Francis, England (Jan. 2014).

Wakankar, A., et al., "Analytical methods for physicochemical characterization of antibody drug conjugates," MABS 3(2): 161-72, Taylor & Francis, England (2011).

EPO Communication for EP Application No. 15837813.3, European Patent Office, Germany, dated Mar. 19, 2019.

Non-Final Office Action dated Nov. 24, 2017, in U.S. Appl. No. 14/843,769, Payne, G., et al., filed Sep. 2, 2015.

Senter, P.D., "Potent antibody drug conjugates for cancer therapy," Current Opinion in Chemical Biology 13:235-244, Elsevier Science Ltd., England (2009).

Grünberg, J., et al. "DOTA-Functionalized Polylysine: A High Number of DOTA Chelates Positively Influences the Biodistribution of Enzymatic Conjugated Anti-Tumor Antibody chCE7agl," PloS One 8(4):e60350, Public Library of Science, United States (Apr. 2013).

Perez, H.L., et al. "Antibody-drug conjugates: current status and future directions," Drug Discovery Today 19(7):869-81, Elsevier Science Ltd., England (Nov. 2013).

Sochaj, A.M., et al. "Antibody-drug conjugates: current status and future directions," Biotechnology Advances 33; 775-784, Elsevier Science Ltd., England (May 2015).

(56) References Cited

OTHER PUBLICATIONS

Whiteman, K.R., et al. "IMGN779: A CD33-Targeted Antibody-Drug Conjugate (ADC) Utilizing a Novel DNA Alkylator, DGN462, is Highly Active in vitro against Primary Patient AML Cells and in vivo against AML Xenografts in Mice," Haematologica, the Homatology Journal: Official Organ of the European Hematology Association, 99, Suppl. 1, p. 293 (Jun. 2014).

Extended European Search Report for European Application No. 17001799.0, Munich, Germany, dated Mar. 20, 2018, 14 pages.

Dependence of Cytotoxic Potency on huMov19-sulfo-SPDB-DM4 MAR

Dependence of Cytotoxic Potency on huMov19-sulfo-SPDB-DM4 concentration

Figure 4
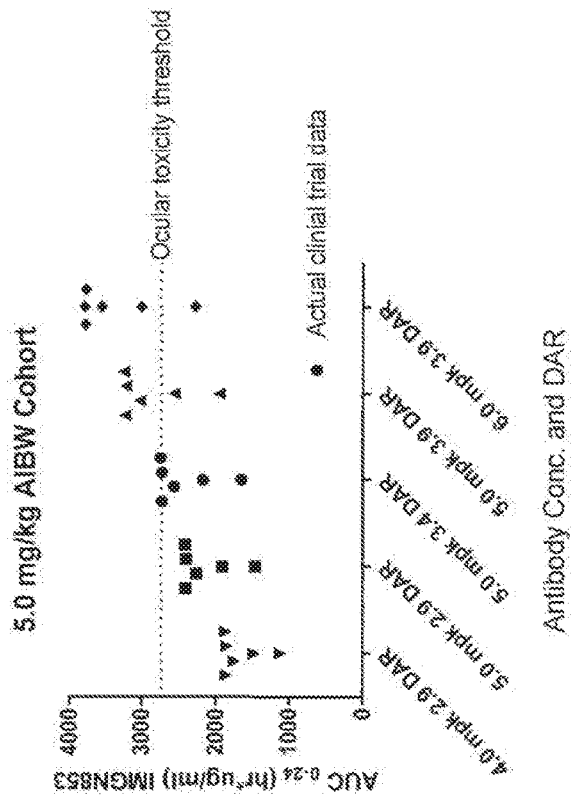
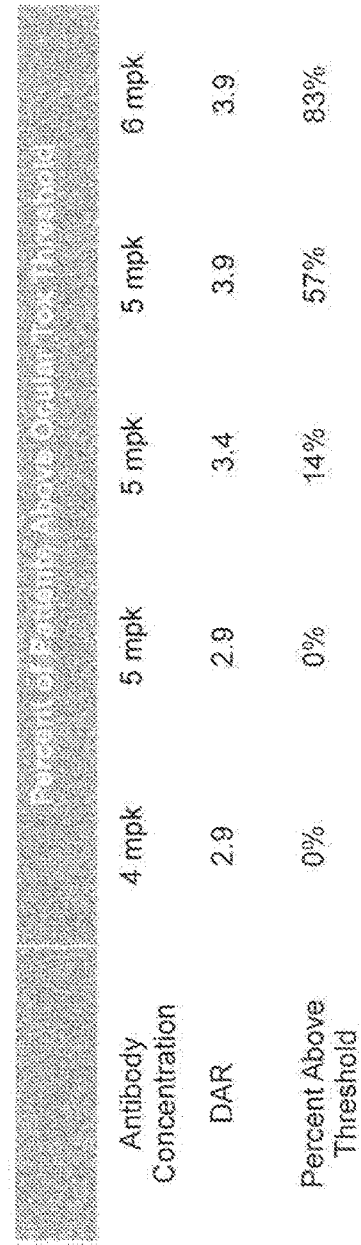

Figure 5
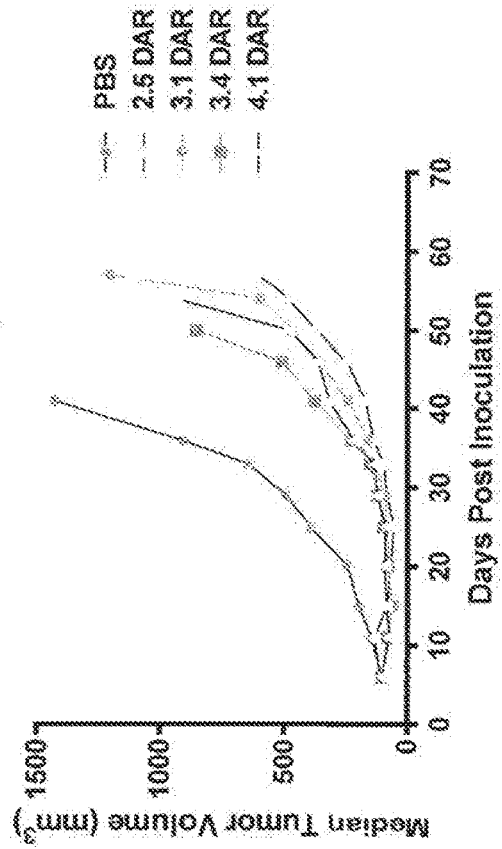
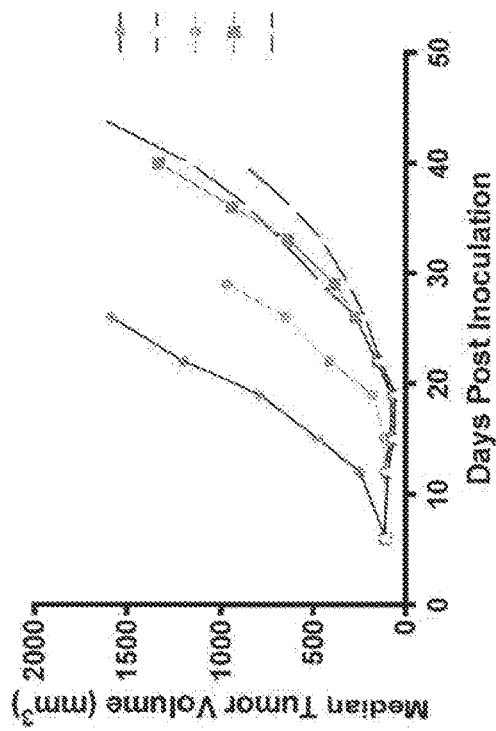

Impact of DAR on MTD of huMov19-sulfo-SPDB-DM4

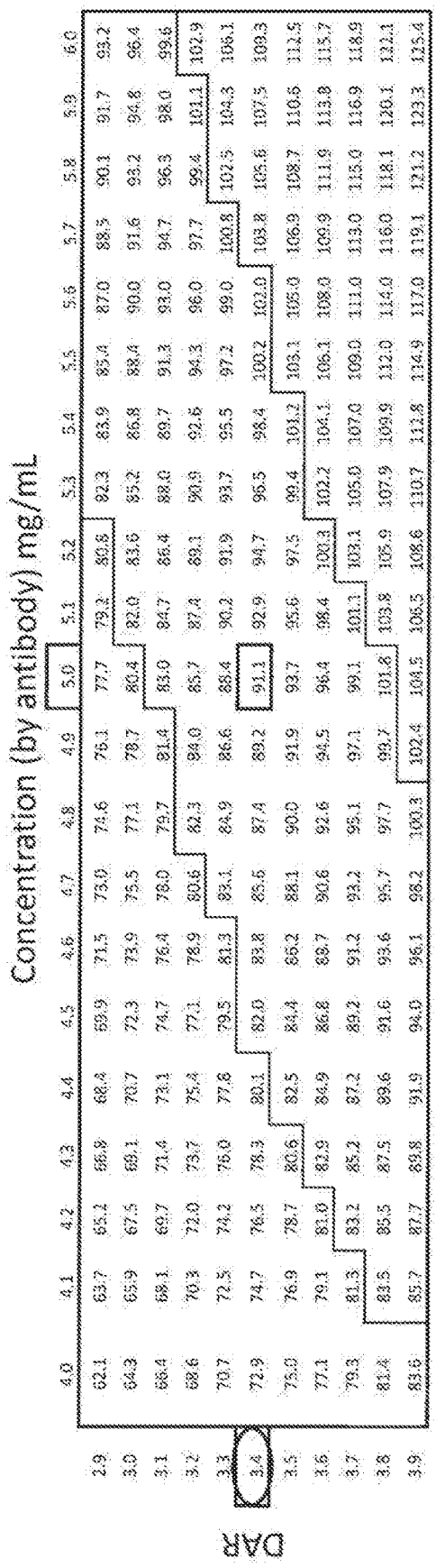
Figure 9A: Advantage of preparing an ADC composition based on DM4 concentration
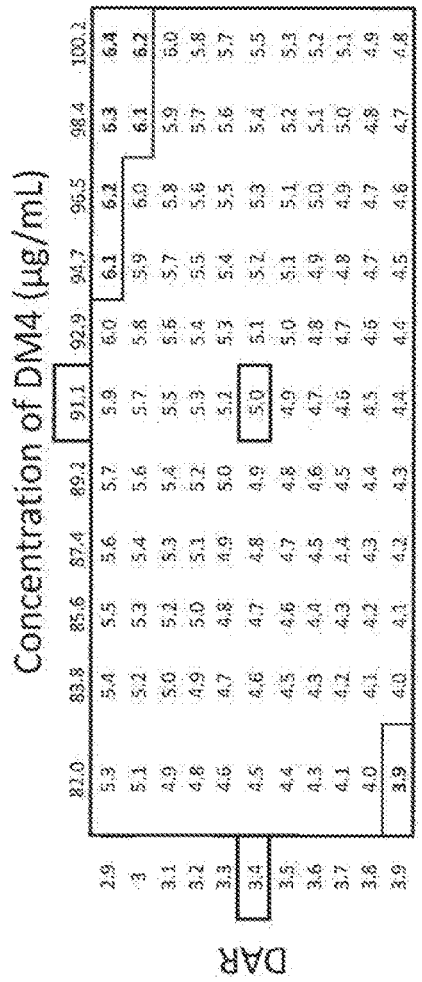
Figure 9B: Antibody concentration specification fails at the high-low extremes

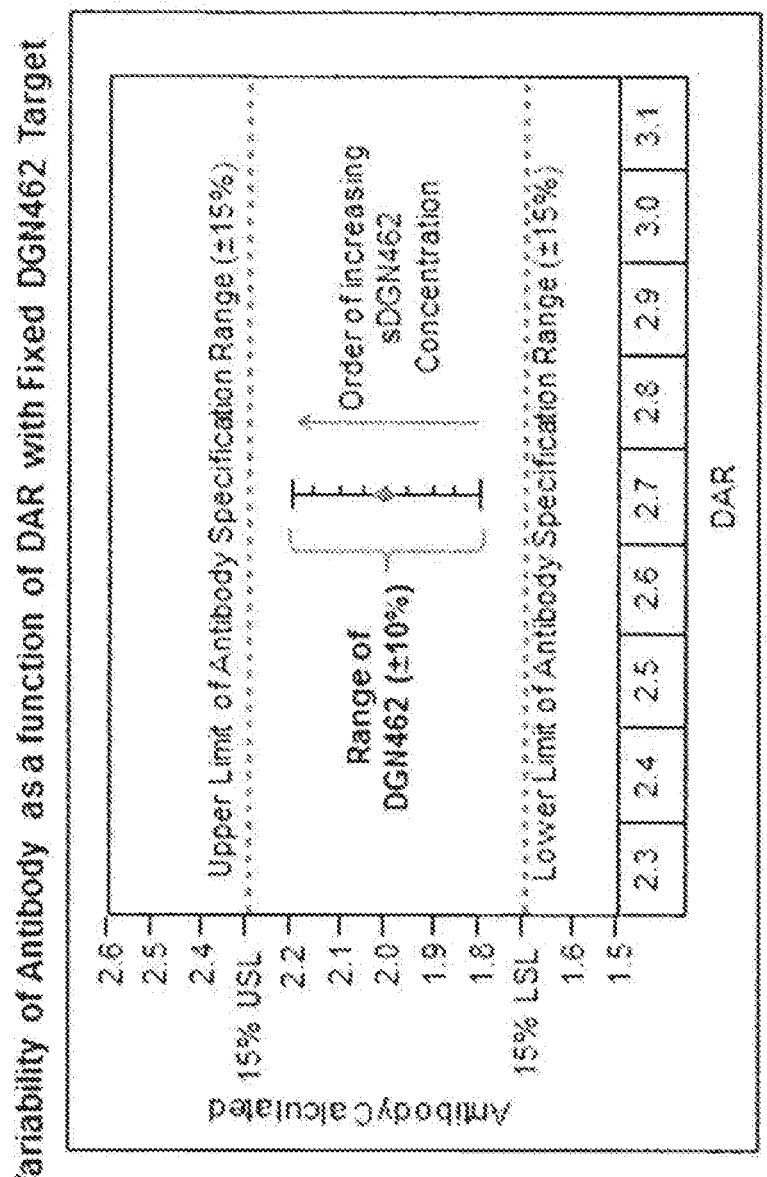
Figure 10A Effect of Preparing an ADC composition by Fixed DGN462 on Antibody Concentration

METHODS FOR FORMULATING ANTIBODY DRUG CONJUGATE COMPOSITIONS

CROSS-REFERENCE TO RELATED APPLICATION

This application is a divisional of U.S. patent application Ser. No. 14/843,769, filed Sep. 2, 2015, which claims priority under 35 U.S.C. § 119(e) to U.S. Provisional Patent Application Ser. No. 62/044,592, filed Sep. 2, 2014, each of which is herein incorporated by reference in its entirety.

SEQUENCE LISTING

The instant application contains a Sequence Listing which has been submitted electronically in ASCII format and is hereby incorporated by reference in its entirety. Said ASCII copy, created on May 8, 2019, is named 2921_0910003_Sequence_Listing_st25.txt and is 49,749 bytes in size.

BACKGROUND OF THE INVENTION

Antibodies that specifically hind tumor surface antigens are used to deliver cytotoxic drugs in the form of antibody drug conjugates (ADCs). Cytotoxic drugs are typically conjugated to antibodies at cysteine or lysine residues. The number of molecules of a drug conjugated per antibody, also termed the drug-to-antibody ratio ("DAR"), is typically a distribution of species ranging from 0-8. The DAR for a manufacturing batch of ADC is determined empirically using spectrophotometric measurements and ADC therapeutic compositions typically contain a mixture of ADC species that differ in drug load. Thus, the DAR for an ADC batch represents the average DAR of the ADC species within the hatch.

ADC cancer therapeutics and antibody cancer therapeutics are both formulated based on nominal antibody protein concentration and must conform to specification. While the drug product label gives information about the "nominal" or target protein concentration, the drug concentration in the vial may vary relative to the target antibody concentration because of the allowed variation in DAR, even while conforming to the acceptance criteria. The potency of ADCs is generally linear relative to concentration. Unlike antibodies, ADCs have an additional potential for variable potency due to the DAR. A typical specification for antibody concentration and DAR allows the concentration of cytotoxic drug in the ADC product vial to vary somewhat from batch-to-batch when patient dosing is based on nominal antibody concentration.

It is important that patients receive an ADC dose that is both safe and effective. Improved methods of formulating ADC compositions would advantageously reduce variability in potency, efficacy, and/or toxicity between batches and ensure that patients receive an ADC within the intended therapeutic range.

SUMMARY OF THE INVENTION

The current invention provides a novel method for formulating a therapeutic composition comprising an antibody drug conjugate ("ADC") based on drug concentration, thereby narrowing variability in potency between batches of ADC, minimizing toxicity and increasing the efficacy of drug formulated according to this method.

The invention is based, at least in part, on the discovery that the efficacy and toxicity of some ADCs is driven entirely or predominantly by the concentration of drug administered rather than by antibody concentration. Conventional methods of formulating an antibody based therapeutic, including ADC containing pharmaceutical compositions, have relied on dosing the patient based on antibody concentration. While this might be advantageous to compositions that only contain an antibody, formulating ADCs using antibody concentrations can cause the drug concentrations to vary and potentially fall outside the desired range. The potency of ADCs is generally linear relative to concentration of the attached drug which can be affected by both the antibody concentration and the DAR as illustrated by the formula [drug]=DAR*[Antibody]. The DAR, antibody and drug each vary within a given and acceptable range, as defined by a given ADC specification. However, because the drug and antibody are attached, the variability of one component affects the other. For example, a variability of ±10-20% in the antibody concentration, which is within the acceptable range by industry standards, would cause a ±10-20% variation in the drug concentration which can cause a ±20-40% variability of potency of the drug product in the vial. A ±15% variation in DAR would add further variation in potency as it would allow 15% higher or lower concentrations of drug. This effect can be particularly relevant for a specific subset of ADCs where it has been demonstrated that the concentration of the drug is the main driver of the toxicity and efficacy.

ADCs are linked to cytotoxic agents, also known as "drug" molecules and the number of drug molecules conjugated per antibody molecule is represented by the term 'drug-to-antibody' ratio ("DAR"). The DAR for a manufacturing batch of ADC is determined empirically using spectrophotometric measurements by obtaining the ratio of concentration of drug to that of antibody. The DAR for a particular batch of ADC represents an average number of drugs attached to each antibody molecule within that batch. Typical DAR specifications for clinical development are in the range of ±10-15%. Conventionally, the initial step in an ADC formulation is to determine the molar concentration for both the drug and the antibody and to calculate the DAR. The ADC is then formulated to a target antibody concentration allowing the drug concentration to vary according to the manufactured DAR value, as follows:

$$[drug]=DAR*[Antibody].$$

In contrast, the present invention is based on the discovery that, by formulating the ADC composition based on a target drug concentration defined at a fixed antibody concentration and fixed DAR, the variability in potency and toxicity can be minimized. Therefore, in cases where it has been demonstrated that the potency, efficacy and/or toxicity of the ADC are primarily driven by the amount of drug administered, improved methods for reducing variability of the cytotoxic drug concentration would be beneficial. Accordingly, the formulation methods described below include determining target drug concentration at a fixed antibody concentration and a fixed DAR and formulating the antibody drug conjugate composition to achieve the target drug concentration. Such improved formulation methods ensure that patients are dosed within a narrow intended drug range without additional risk of batch failure.

In one aspect, the invention generally provides a method of reducing (e.g., by at least about 5%, 10%, 20% or more) potency variability in an antibody drug conjugate composition, the method involving determining target drug concentration at a fixed antibody concentration and drug antibody ratio; and formulating the antibody drug conjugate composition to achieve the target drug concentration, thereby reducing potency variability in the composition. In one embodiment, the variability in the drug concentration is about ±10%. In various embodiments, the variability is less than about ±5, 6, 7, 8, or 9%. In one embodiment, the method reduces batch-to-batch potency variation (e.g., by at least about 5%, 10%, 20%, 25%, 30%, 35%, 40%, 45%, 50%, or more). It should be noted that when the variation is represented as ±, it is intended to describe a variation of a specific % higher or lower than the specified value. When the variation is represented as a single total value (e.g., at least 10%) it is intended to represent the difference between the maximum and the minimum potential values. In another embodiment, the composition is a finished drug product. In yet another embodiment, the drug concentration varies within the antibody specification concentration. In one embodiment, the antibody concentration is equal to target antibody concentration ± less than about 1, 2, 3, 4, 5, 6, 7, 8, 9, or 10%. In another embodiment, antibody concentration is equal to target antibody concentration ± less than about 10%, 12%, 15%, or 20%.

In another distinct aspect, the invention provides a method of reducing potency variability in a composition comprising an antibody drug conjugate. The method involves formulating the antibody drug conjugate by targeting a variable drug concentration which falls in the midpoint of the range where the antibody concentration specification range and the drug concentration specification range overlap, thereby reducing potency variability in the composition. In this regard, the invention provides a method of reducing potency variability in a composition containing an antibody drug conjugate involving: (a) measuring the DAR for the antibody drug conjugate composition; (b) determining the upper antibody specification limit and the lower antibody specification limit, where the upper antibody specification limit is the target antibody concentration plus the maximum variation allowed by the specification and the lower antibody specification limit is the target antibody concentration minus the maximum variation allowed by the specification; (c) determining the defined upper drug specification limit and the defined lower drug specification limit, where the defined upper drug specification limit is the target drug concentration plus the maximum variation allowed by the specification and the defined lower drug specification limit is the target drug concentration minus the maximum variation allowed by the specification; (d) determining the calculated upper drug specification limit (USL (drug)) as follows:

$$USL(\text{drug})\,\mu g/mL = \frac{\text{Upper Antibody Concentration Specification Limit} \times DAR \times \text{Drug Mol. Wt.}}{\text{Antibody Mol. Wt.}} \times 1000$$

(e) determining the calculated lower drug specification limit (LSL (drug)) as follows:

$$LSL(\text{drug})\,\mu g/mL = \frac{\text{Lower Antibody Concentration Specification Limit} \times DAR \times \text{Drug Mol. Wt.}}{\text{Antibody Mol. Wt.}} \times 1000$$

(f) comparing the calculated USL (drug) of step (d) to the defined upper drug specification limit of step (c), and selecting the lower of the two values as the effective upper drug specification limit; (g) comparing the calculated LSL (drug) of step (e) to the defined lower drug specification limit of step (c), and selecting the higher of the two values as the effective lower drug specification limit; and (h) formulating the antibody drug conjugate composition to a target drug concentration that is the midpoint between the effective upper drug specification limit and the effective lower drug specification limit, thereby reducing potency variability in the composition. In one embodiment, the method narrows the range of the upper and lower specification limits for the drug to about ±3-9%. In another embodiment, the method narrows the range of the upper and lower specification limits for the drug to about ±4%. In one embodiment, the maximum variation allowed by the specification in step (b) is about ±15%. In another embodiment, the maximum variation allowed by the specification in step (b) is less than about ±10, 11, 12, 13, or 14%. In one embodiment, the maximum variation allowed by the specification in step (c) is about ±15%. In another embodiment, the maximum variation allowed by the specification in step (c) is less than about ±10, 11, 12, 13, or 14%. In various embodiments, the antibody is a non-functional antibody. In various embodiments, the DAR is at the lower limit of DAR specification or at the upper limit of DAR specification. In various embodiments, the lower limit of DAR specification is 2.3, 2.4, or 2.5. In various embodiments, the upper limit of DAR specification is 2.9, 3.0, or 3.1.

In a related aspect, for example where the antibody is a functional antibody, the invention also provides a method of formulating an antibody drug conjugate by targeting a variable antibody concentration which falls in the midpoint of the range where the antibody concentration specification range and the drug concentration specification range overlap, thereby targeting an antibody concentration that will allow the least fluctuation in the drug concentration when the ADC is formulated. This allows for tighter control of the antibody concentration in the ADC formulation.

In another aspect, the invention provides a method of formulating an antibody drug conjugate composition, the method involving determining target drug concentration at a fixed antibody concentration and drug antibody ratio; and formulating the antibody drug conjugate composition to achieve the target drug concentration.

In yet another aspect, the invention provides a method of reducing potency variability in a composition comprising an antibody maytansinoid conjugate, the method involving determining target maytansinoid concentration at a fixed antibody concentration and maytansinoid-to-antibody ratio; and formulating the antibody maytansinoid conjugate composition to achieve the target maytansinoid concentration, thereby reducing potency variability in the composition.

In yet another aspect, the invention provides a method of formulating an antibody maytansinoid conjugate composition, the method involving determining target maytansinoid concentration at a fixed antibody concentration and maytansinoid-to-antibody ratio; and formulating the antibody maytansinoid conjugate composition to achieve the target maytansinoid concentration.

In yet another aspect, the invention provides a method of formulating an antibody benzodiazepine (e.g., pyrrolobenzodiazepine or indolinobenzodiazepine) conjugate composition, the method involving determining target benzodiazepine concentration at a fixed antibody concentration and benzodiazepine-to-antibody ratio; and formulating the antibody benzodiazepine conjugate composition to achieve the target benzodiazepine concentration.

In another distinct aspect, the invention provides a method of reducing potency variability in a composition containing an antibody benzodiazepine (e.g., pyrrolobenzodiazepine or indolinobenzodiazepine) conjugate involving: (a) measuring the DAR for the antibody benzodiazepine (e.g., pyrrolobenzodiazepine or indolinobenzodiazepine) conjugate composition; (b) determining the upper antibody specification limit and the lower antibody specification limit, where the upper antibody specification limit is the target antibody concentration plus the maximum variation allowed by the specification and the lower antibody specification limit is the target antibody concentration minus the maximum variation allowed by the specification; (c) determining the defined upper benzodiazepine specification limit and the defined lower benzodiazepine specification limit, where the defined upper benzodiazepine specification limit is the target benzodiazepine concentration plus the maximum variation allowed by the specification and the defined lower benzodiazepine specification limit is the target benzodiazepine concentration minus the maximum variation allowed by the specification; (d) determining the calculated upper benzodiazepine specification limit (USL (drug)) as follows:

$$USL(\text{drug})\,\mu g/mL = \frac{\text{Upper Antibody Concentration Specification Limit} \times \frac{DAR \times \text{Drug Mol. Wt.}}{\text{Antibody Mol. Wt.}}}{} \times 1000$$

(e) determining the calculated lower benzodiazepine specification limit (LSL(drug)) as follows:

$$LSL(\text{drug})\,\mu g/mL = \frac{\text{Lower Antibody Concentration Specification Limit} \times \frac{DAR \times \text{Drug Mol. Wt.}}{\text{Antibody Mol. Wt.}}}{} \times 1000$$

(f) comparing the calculated USL (drug) of step (d) to the defined upper benzodiazepine specification limit of step (c), and selecting the lower of the two values as the effective upper benzodiazepine specification limit; (g) comparing the calculated LSL (drug) of step (e) to the defined lower benzodiazepine specification limit of step (c), and selecting the higher of the two values as the effective lower benzodiazepine specification limit; and (h) formulating the antibody benzodiazepine conjugate composition to a target benzodiazepine concentration that is the midpoint between the effective upper benzodiazepine specification limit and the effective lower benzodiazepine specification limit, thereby reducing potency variability in the composition.

In still another aspect, the invention provides a method for dosing a subject within a narrow intended range, the method involves providing an antibody drug conjugate composition formulated according to the method of any previous aspect, and administering said composition to the subject.

In yet another aspect, the invention provides a pharmaceutical composition containing an antibody drug conjugate formulated according to the method of a previous aspect, where a nominal drug (e.g., maytansinoid, benzodiazepine compounds, auristatin) concentration is provided on the label.

In various embodiments of any previous aspect or any other aspect of the invention described herein, the drug is a cytotoxic agent. Cytotoxic agents include, without limitation, tubulin inhibitors, DNA damaging agents, DNA cross linkers. DNA alkylating agents, and cell cycle or mitotic disrupters. Non-limiting examples of cytotoxic agents include maytansinoids; benzodiazepine compounds, such as pyrrolobenzodiazepines and indolinobenzodiazepines; and auristatins). In particular embodiments of the previous aspects, the method reduces batch-to-batch potency variation (e.g., by at least about 5%, 10%, 20%, 25%, 30%, 35%, 40%, 45%, 50% or more). In other embodiments, the composition is a finished drug product. In yet other embodiments, the antibody concentration varies within the antibody specification concentration. In still other embodiments of the previous aspects, the method reduces batch-to-batch potency variability in producing the antibody maytansinoid conjugate. In various embodiments of the previous aspects, the composition is allowed to vary in potency by about 10-40% (e.g., 10, 15, 20, 25, 30, 35, 40%). In other embodiments of the previous aspects, the composition is allowed to vary in potency by about 10-20% (e.g., 10, 12, 15, 18, 20%). In still other embodiments of the above aspects, the antibody concentration specification is equal to target ± less than about 1, 2, 3, 4, 5, 6, 7, 8, 9, or 10%. In other embodiments, antibody concentration specification is equal to target ± less than about 10%, 12%, 15%, or 20%. In various embodiments of the previous aspects, variability in composition potency is reduced relative to when the antibody drug conjugate composition is formulated based on antibody concentration. In various embodiments of the previous aspects, the antibody concentration and conjugated drug (e.g., maytansinoid, benzodiazepine compounds, auristatin) concentration are determined by spectrophotometric measurement. In various embodiments of the previous aspects, drug to antibody ratio is determined by size exclusion chromatography (SEC) or by SEC-mass spectrometry (SEC-MS). In other embodiments of the previous aspects, the efficacy or toxicity of the composition is independent of drug to antibody ratio or antibody concentration, but dependent on the total administered dose of conjugated drug (e.g., maytansinoid, benzodiazepine compounds, auristatin). In still other embodiments of the previous aspects, efficacy of the composition is independent of or largely independent of drug to antibody ratio. In various embodiments of the previous aspects, toxicity of the composition is independent of or largely independent of drug to antibody ratio. In various embodiments of the previous aspects, efficacy or toxicity depends on or largely depends on conjugated drug (e.g., maytansinoid, benzodiazepine compounds, auristatin) concentration. In various embodiments of the previous aspects, efficacy depends on, substantially depends on, or depends at least in part on conjugated drug (e.g., maytansinoid, benzodiazepine compounds, auristatin) concentration. In various embodiments of the previous aspects, toxicity depends, substantially depends, or depends at least in part on conjugated drug (e.g., maytansinoid, benzodiazepine compounds, auristatin) concentration. In various embodiments of the previous aspects, efficacy is independent of, substantially independent of, or is at least in part independent of antibody concentration. In various embodiments of the previous aspects, toxicity is independent of, substantially independent of, or is at least in part independent of antibody concentration. In various embodiments of the previous aspects, efficacy and toxicity depend on, substantially depend on, or depend at least in part on conjugated drug (e.g., maytansinoid, benzodiazepine compounds, auristatin) concentration and on antibody concentration. In various embodiments of the previous aspects, efficacy and toxicity depend less on antibody concentration than on conjugated drug (e.g., maytansinoid, benzodiazepine compounds, auristatin) concentration. In various embodiments of the previous aspects, efficacy depends on, substantially depends on, or depends at least in part on conjugated drug (e.g., maytansinoid, benzodiazepine compounds, auristatin) concentration and on antibody concentration. In various embodiments of the previous aspects, toxicity depends on, substantially depends on, or depends at least in part on conjugated drug (e.g., maytansinoid, benzodiazepine compounds, auristatin) concentration and on antibody concentration. In various embodiments of the previous aspects, efficacy depends on, substantially depends on, or depends at least in part on conjugated drug (e.g., maytansinoid, benzodiazepine compounds, auristatin) concentration and on antibody concentration and toxicity depends on, substantially depends on, or depends at least in part on conjugated drug concentration. In various embodiments of the previous aspects, efficacy depends on, substantially depends on, or depends at least in part on conjugated drug (e.g., maytansinoid, benzodiazepine compounds, auristatin) concentration and on antibody concentration and toxicity depends on, substantially depends on, or depends at least in part on antibody concentration. In various embodiments of the previous aspects, toxicity depends on, substantially depends on, or depends at least in part on conjugated drug (e.g., maytansinoid, benzodiazepine compounds, auristatin) concentration and on antibody concentration and efficacy depends on, substantially depends on, or depends at least in part on conjugated drug (e.g., maytansinoid, benzodiazepine compounds, auristatin) concentration. In various embodiments of the previous aspects, toxicity depends on, substantially depends on, or depends at least in part on antibody concentration and efficacy depends on, substantially depends on, or depends at least in part on conjugated drug (e.g., maytansinoid, benzodiazepine compounds, auristatin) concentration. In various embodiments of the previous aspects, the antibody drug conjugate composition is formulated for infusion. In various embodiments of the previous aspects, the antibody drug conjugate is formulated with a pharmaceutically acceptable parenteral vehicle. In various embodiments of the previous aspects, the antibody drug conjugate is formulated in a unit dosage injectable form.

In various embodiments of any previous aspect or any other aspect of the invention delineated herein, the method comprises determining an upper specification limit (USL) and a lower specification limit (LSL). In certain embodiments, the calculated USL and LSL are determined using the formulae below:

$$USL(\text{drug}) \, \mu g/mL = \\ \frac{\text{Upper Antibody Concentration Specification Limit} \times DAR \times \text{Drug Mol. Wt.}}{\text{Antibody Mol. Wt.}} \times 1000$$

$$LSL(\text{drug}) \, \mu g/mL = \\ \frac{\text{Lower Antibody Concentration Specification Limit} \times DAR \times \text{Drug Mol. Wt.}}{\text{Antibody Mol. Wt.}} \times 1000$$

In other embodiments of any of the above aspects, the cytotoxic compound or drug is a tubulin inhibitor, DNA damaging agent, DNA cross linker, DNA alkylating agent, or cell cycle or mitotic disrupter.

In still other embodiments of any of the above aspects, a drug includes, but is not limited to, maytansinoids and maytansinoid analogs, benzodiazepine compounds (e.g., pyrrolobenzodiazepines and indolinobenzodiazepines; see also Table 1: compounds D1-D10 and DGN462), taxoids, CC-1065 and CC-1065 analogs, duocarmycins and duocarmycin analogs, enediynes, such as calicheamicins, dolastatin and dolastatin analogs including auristatins, tomaymycin derivatives, leptomycin derivatives, methotrexate, cisplatin, carboplatin, daunorubicin, doxorubicin, vincristine, vinblastine, melphalan, mitomycin C, chlorambucil, and morpholino-doxorubicin.

In various embodiments of the previous aspects, the maytansinoid is DM1, DM3, or DM4. In various embodiments of the previous aspects, the benzodiazepine compounds are selected from the representative cytotoxic agents D1-D10 and DGN462 listed in Table 1 below,

TABLE 1

Benzodiazepine compounds

| Compound No. | Structure |
|---|---|
| D1 | 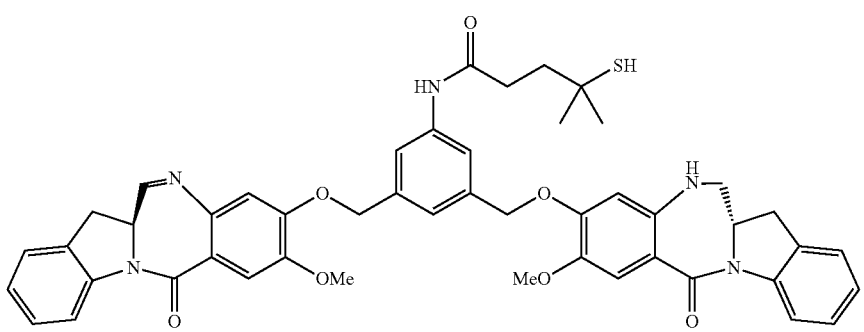 [SMILES: COc1cc2c(cc1OCc1cc(COc3cc4c(cc3OC)C(=O)N3c5ccccc5C[C@H]3CN4)cc(NC(=O)CCC(C)(C)S)c1)N=C[C@@H]1Cc3ccccc3N1C2=O] |

TABLE 1-continued
Benzodiazepine compounds
| Compound No. | Structure |
|---|---|
| D2 | 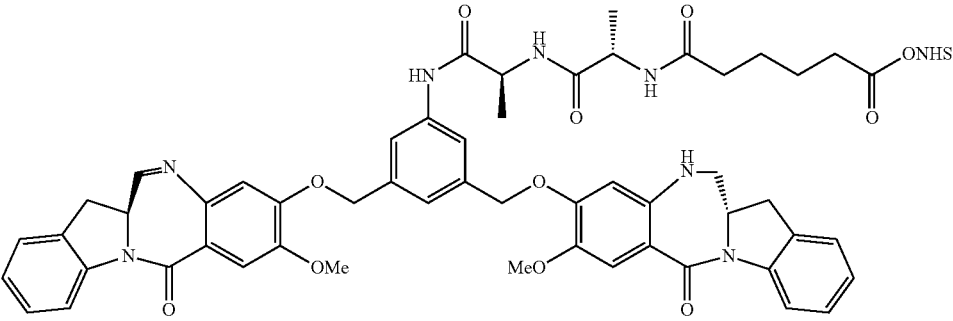 |
| DGN462 | 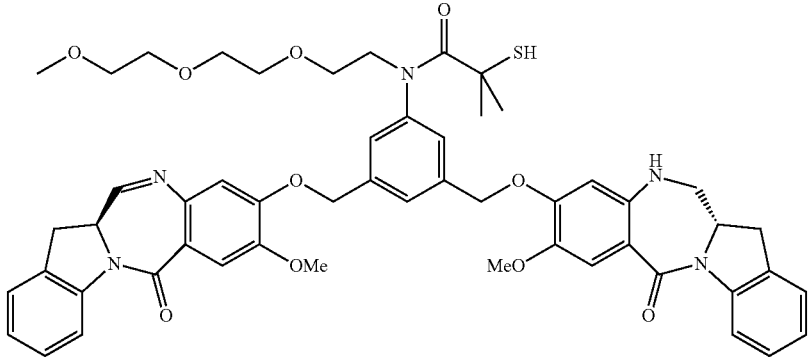 [SMILES: COCCOCCOCCN(C(=O)C(C)(C)S)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1] |
| D3 | 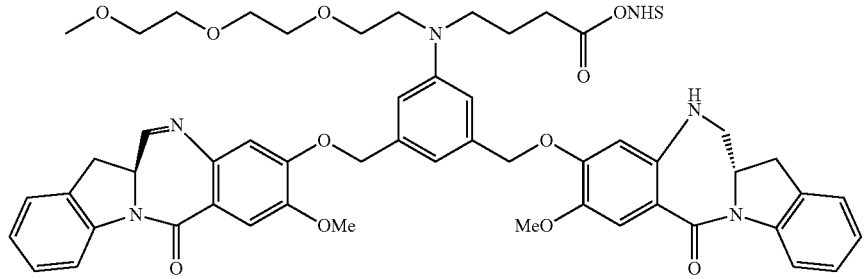 |
| D4 | 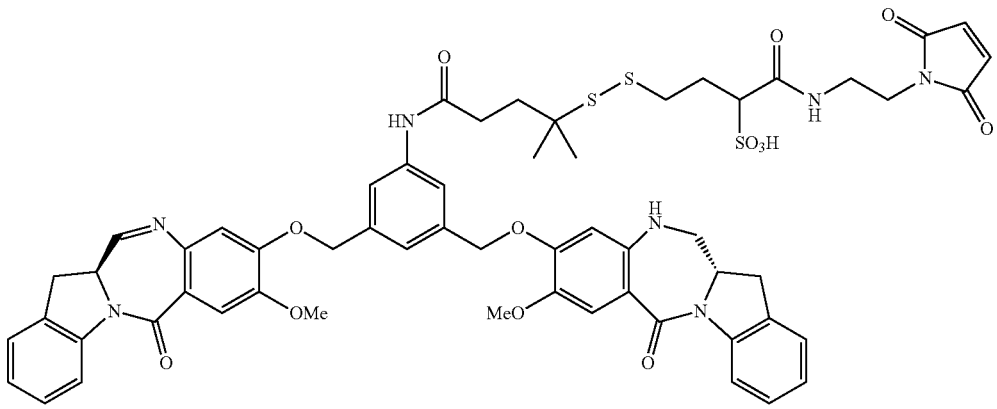 [SMILES: COc1cc2c(cc1OCc1cc(COc3cc4c(cc3OC)C(=O)N3c5ccccc5C[C@H]3CN4)cc(NC(=O)CCC(C)(C)SSCCC(C(=O)NCCN3C(=O)C=CC3=O)S(=O)(=O)O)c1)N=C[C@@H]1Cc3ccccc3N1C2=O] |

TABLE 1-continued
Benzodiazepine compounds
| Compound No. | Structure |
|---|---|
| D5 | 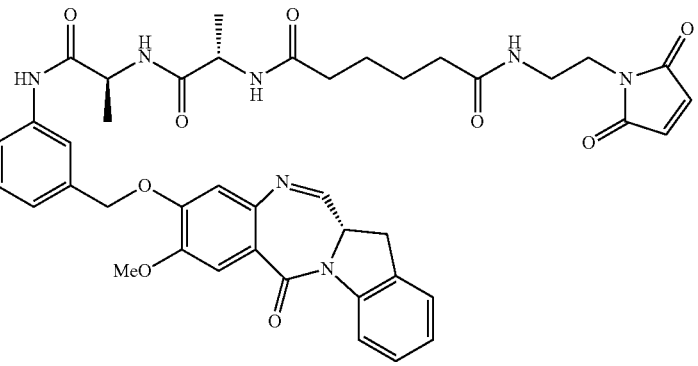 |
| D6 | 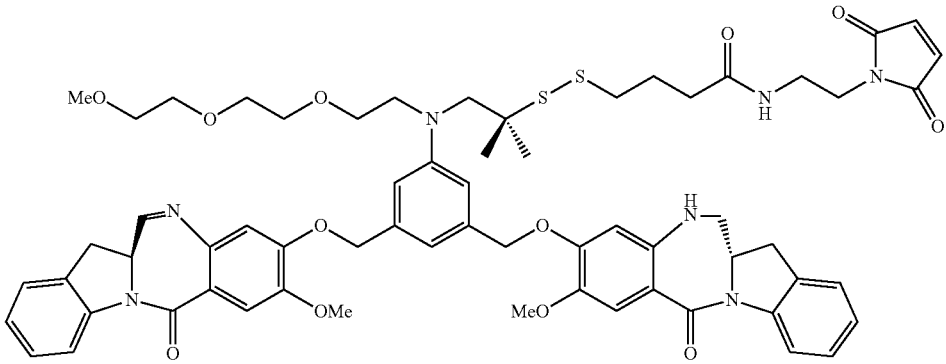 |
| D7 | 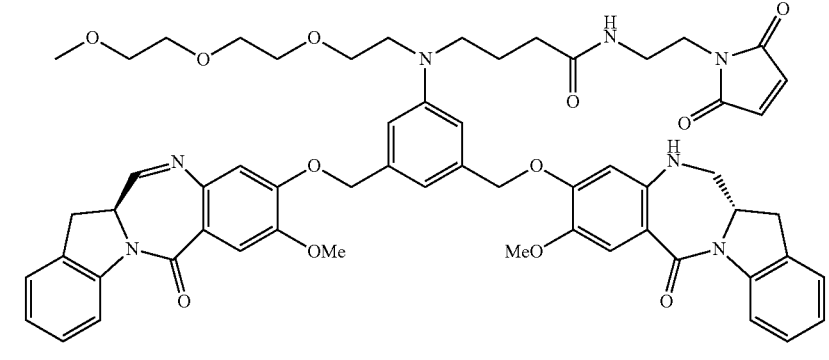 [SMILES: COCCOCCOCCN(CCCC(=O)NCCN1C(=O)C=CC1=O)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1] |
| D8 | 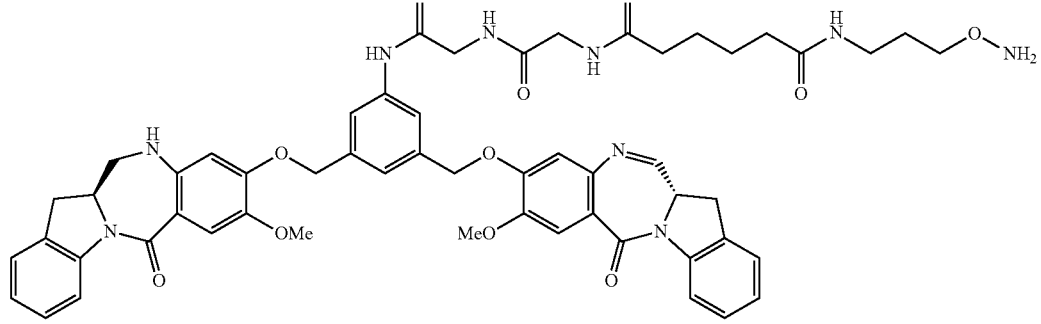 |

TABLE 1-continued

Benzodiazepine compounds

| Compound No. | Structure |
|---|---|
| D9 | 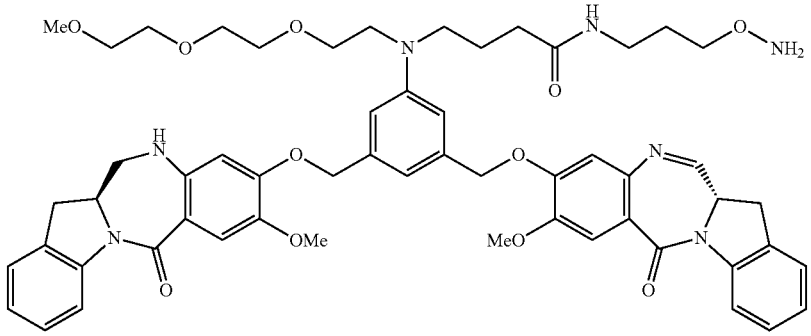 [SMILES: COCCOCCOCCN(CCCC(=O)NCCCON)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1] |
| D10 | 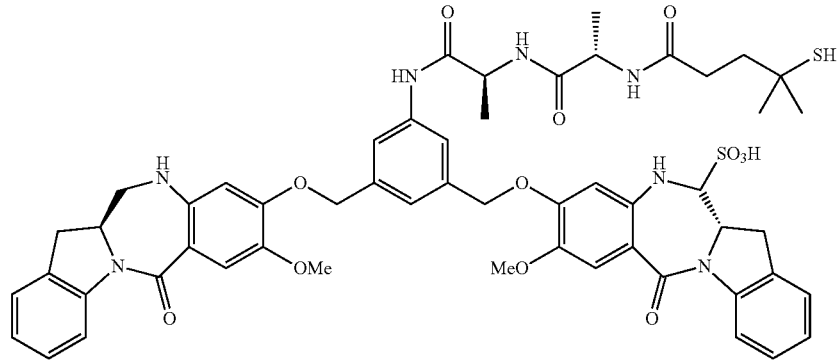 |

Note that other variations (e.g., sulfonated versions) of the compounds listed in Table 1 are also contemplated and will readily be apparent to one of skill in the art.

In various embodiments of the previous aspects, the antibody may be a functional antibody or non-functional antibody. Non-functional antibodies include, for example, huDS6 and antibodies with only effector-mediated cell killing, such as huMov19 (M9346A), huAnti-CD 123, huMy9-6 (Z4681A), and huB4. Functional antibodies include, for example, huEGFR-7R and huCD37-3. In certain embodiments, the drug is a benzodiazepine compound and the antibody is a non-functional antibody. In certain embodiments, the drug is a maytansinoid and the antibody is a non-functional antibody.

In various embodiments of the previous aspects, the linker is a cleavable linker, such as N-succinimidyl 3-(2-pyridyldithio) propionate (SPDP), N-succinimidyl 4-(2-pyridyldithio)butanoate (SPDB), N-succinimidyl 4-(2-pyridyldithio) 2-sulfobutanoate (sulto-SPDB), or N-succinimidyl 4-(2-pyridyl dithio)pentanoate (SPP). In various embodiments of the previous aspects, the linker is a non-cleavable linker, such as 2-iminothiolane, acetylsuccinic anhydride, succinimidyl 4-(maleimidomethyl)cyclohexanecarboxylate (SMCC). The generic linkers 2-iminothiolane and acetylsuccinic anhydride can be used as cleavable or non-cleavable linkers.

In various embodiments of the previous aspects, the linker antibody drug conjugate is huMov19-sulfo-SPDB-DM4, huMov19-sulfo-SPDB-D1, huMov19-D2, huMov19-sulfo-SPDB-D10, huMov19-sulfo-SPDB-DGN462, huMy9-6-sulfo-SPDB-D1, huMy9-6-D2, huMy9-6-sulfo-SPDB-D 10, huMy9-6-sulfo-SPDB-DGN462, huAnti-CD123-sulfo-SPDB-D1, huAnti-CD123-D2, huAnti-CD123-sulfo-SPDB-D10, huAnti-CD123-sulfo-SPDB-DGN462, huB4-SPDB-DM4, huDS6-SPDB-DM4, huCD37-3-SMCC-DM1, huCD37-50-SMCC-DM1, or huEGFR-7R-SMCC-DM1.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham. The Harper Collins Dictionary of Biology (1991). As used herein, the following terms have the meanings ascribed to them below, unless specified otherwise.

The term "adjusted ideal body weight (AIBW)" refers to a size descriptor that accounts for sex, total body weight, and height. AIBW can be calculated, for example, using the formula AIBW=IBW+0.4(weight in kg−IBW) where:

Ideal Body Weight (IBW)
1. $IBW^1$ (male)=$0.9H^1$-88
2. $IBW^1$ (female)=$0.9H^1$-92.
($^1$H=height in cm; W=weight in kg)

IBW, LBW, and ADJ are discussed in more detail in Green and Duffull, *British Journal of Clinical Pharmacology* 58: 119-133 (2004), which is herein incorporated by reference in its entirety.

By "cytotoxic agent" is meant a small molecule chemical compound, peptide, or nucleic acid molecule that is toxic to cells. In some embodiments described herein, for ease of reference, the term "drug" is used to refer to a cytotoxic agent. For example, in an antibody drug conjugate (an ADC), the term "drug" is used interchangeably with the term "cytotoxic agent." In particular embodiments, the cytotoxic agent (or "drug") is conjugated to an antibody. In one particular embodiment, the cytotoxic agent is a maytansinoid, such as DM1, DM3, or DM4. In other embodiments, cytotoxic agents include, but are not limited to, benzodiazepine compounds (e.g., pyrrolobenzodiazepines and indolinobenzodiazepines; see also Table 1: compounds D1-D10 and DGN462), taxoids, CC-1065 and CC-1065 analogs, duocarmycins and duocarmycin analogs, enediynes, such as calicheamicins, dolastatin and dolastatin analogs including auristatins, tomaymycin derivatives, leptomycin derivatives, methotrexate, cisplatin, carboplatin, daunorubicin, doxorubicin, vincristine, vinblastine, melphalan, mitomycin C, chlorambucil, and morpholino-doxorubicin.

By "drug-to-antibody ratio (DAR)" is meant the average number of "drug" (i.e., cytotoxic agent) molecules conjugated per antibody. DAR is characterized using any method known in the art including, but not limited to, spectroscopy, dynamic light scattering, size exclusion chromatography (SEC), size exclusion chromatography coupled with mass spectrometry (SEC-MS) and mass spectrometry.

By "maytansinoid-to-antibody ratio (MAR)" is meant the average number of maytansinoid molecules conjugated per antibody.

By "target antibody concentration" is meant a desired antibody concentration.

By "target drug concentration" or "target cytotoxic agent concentration" is meant a desired concentration of a drug or cytotoxic agent. It should be noted that the concentration of drug or cytotoxic agent is predominantly calculated based on the conjugated form of the drug but may include minor amounts of free or unconjugated drug found in the sample.

By "target maytansinoid concentration" is meant a desired concentration of maytansinoid.

By "potency variability" is meant the different potencies present in different batches of drug product. Potency variability is desirably reduced by at least about 5%, 10%, 20%, 25%, 30%, 40%, 50% or more.

By "drug product" is meant a finished dosage form that contains an active pharmaceutical ingredient. In one embodiment, a finished drug product is a container (e.g., vial) that contains an antibody drug conjugate of the invention, alone or in combination with an excipient.

By "specification" is meant a set of criteria to which a drug or drug product must conform to be acceptable for its intended use. A specification is typically proposed by a manufacturer and agreed to by a regulatory body (e.g., the FDA).

As used herein, "functional antibody" is meant to refer to an antibody that affects cell death by a direct cell killing mechanism, such as apoptosis or necrosis. Functional antibodies have direct cell killing activity in vivo without being conjugated to a drug ("naked antibody"). Non-limiting examples of functional antibodies include the huEGFR-7R antibody and the huCD37-3 antibody. As used herein, "non-functional antibody" is meant to refer to an antibody that has (i) no known cell killing activity in vivo (e.g., no direct or indirect cell killing as a naked antibody, for example, huDS6) or (ii) indirect cell killing activity as a result of effector function, for example, antibody-dependent cell-mediated cytotoxicity (ADCC), antibody dependent cellular phagocytosis (ADCP) and complement dependent cytotoxicity (CDC), or (iii) has increased conjugate activity in vivo when effector function is increased or any combination of (i), (ii), and (iii). A non-functional antibody may have anti-proliferative activity, for example, by blocking binding of a proliferative agent (e.g., growth factor). Non-limiting examples of non-functional antibodies that have indirect cell killing activity include huMov19, huMy9-6, and huB4.

By "huB4" is meant a humanized antibody or epitope binding fragment thereof that specifically binds CD19, such as human CD19. An exemplary huB4 antibody of the invention may include the following CDRs (shown in bold and underline) or the following light chain (LC) and heavy chain (HC) sequences:

huB4 LC (SEQ ID NO: 1)
EIVLTQSPAIMSASPGERVTMTCSASSGVNYMHWYQQKPGTSPRRWIYDT

SKLASGVPARFSGSGSGTDYSLTISSMEPEDAATYYCHQRGSYTFGGGTK

LEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSS

PVTKSFNRGEC huB4 HC (SEQ ID NO: 2)
QVQLVQPAGEVKKPGASVKLSCKTSGYTFTSNWMHWVKQAPGQGLEWIGE

IDPSDSYTNYNQNFQGKAKLTVDKSTSTAYMEVSSLRSDDTAVYYCARGS

NPYYYAMDYWGQGTSVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK

By "huB4-SPDB-DM4" is meant an antibody drug conjugate that includes an huB4 antibody, which specifically binds CD19, conjugated to the cytotoxic maytansinoid, $N^{2'}$-deacetyl-$N^{2'}$-(4-mercapto-4-methyl-1-oxopentyl) maytansine (DM4) via the linker N-succinimidyl 4-(2-pyridyldithio)butanoate (SPDB), huB4-SPDB-DM4 is described, for example, in U.S. Pat. No. 8,435,528 and International Pat. Appl. Publication No. WO2004/103272, which are incorporated herein by reference in their entireties.

By "huMov19" (also termed "M9346A") is meant a humanized antibody or epitope binding fragment thereof that specifically binds folate receptor alpha (also known as folate receptor 1 or "FOLR1" herein). Detailed sequences for huMov19 are described in U.S. Pat. Nos. 8,557,966 and 8,709,432 and International Pat. Appl. Publication Nos.: WO2011/106528, which are incorporated herein by reference in their entireties. Exemplary huMOV19 antibodies of the invention may include the following CDRs (shown in bold and underline) or the following light chain (LC) and heavy chain (HC) sequences:

huMov19 LC v1.00

(SEQ ID NO: 3)
DIVLTQSPLSLAVSLGQPAIISCKASQSVSFAGTSLMHWYHQKPGQQPRL
LIYRASNLEAGVPDRFSGSGSKTDFTLNISPVEAEDAATYYCQQSREYPY
TFGGGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC huMov19 LC v1.60

(SEQ ID NO: 4)
DIVLTQSPLSLAVSLGQPAIISCKASQSVSFAGTSLMHWYHQKPGQQPRL
LIYRASNLEAGVPDRFSGSGSKTDFTLTISPVEAEDAATYYCQQSREYPY
TFGGGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC huMov19 HC (SEQ ID NO: 5)
QVQLVQSGAEVVKPGASVKISCKASGYTFTGYFMNWVKQSPGQSLEWIGR
IHPYDGDTFYNQKFQGKATLTVDKSSNTAHMELLSLTSEDFAVYYCTRYD
GSRAMDYWGQGTTVTVSSASKTGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVY
TLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG

By "huMov19-sulfo-SPDB-DM4" (also termed "IMGN853") is meant an antibody drug conjugate that comprises an huMov19 antibody, which specifically binds FOLR1, conjugated to the cytotoxic maytansinoid, $N^{2'}$-deacetyl-$N^{2'}$-(4-mercapto-4-methyl-1-oxopentyl) maytansine (DM4) via the disulfide-containing linker N-succinimidyl 4-(2-pyridyldithio)-2-sulfobutanoate (sSPDB). The ADC huMov19-sulfo-SPDB-DM4 is described, for example, by Ab et al., AACR; Cancer Res 2011; 71(8 Suppl): Abstract number 4576, and U.S. Pat. Nos. 8,557,966 and 8,709,432 and International Pat. Appl. Publication Nos.: WO2011/106528 which are each incorporated herein by reference in their entirety.

By "huDS6" is meant a humanized antibody or epitope binding fragment thereof that specifically binds a CA6 sialoglycotope on the Muc1 mucin receptor (e.g., human Muc1) expressed by cancerous cells. Exemplary sequences for huDS6 are described in U.S. Pat. No. 7,834,155 and International Pat. Appl. Publication Nos.: WO2005/009369 and WO2007/024222, which are incorporated herein by reference in their entireties. An exemplary huDS6 antibody of the invention may include or consists of the following CDRs (shown in bold and underline) or the following light chain (LC) and heavy chain (HC) sequences:

huDS6 LC (SEQ ID NO: 6)
EIVLTQSPATMSASPGERVTITCSAHSSVSFMHWFQQKPGTSPKLWIYST
SSLASGVPARFGGSGSGTSYSLTISSMEAEDAATYYCQQRSSFPLTFGAG
TKLELKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC huDS6 HC (SEQ ID NO: 7)
QAQLVQSGAEVVKPGASVKMSCKASGYTFTSYNMHWVKQTPGQGLEWIGY
IYPGNGATNYNQKFQGKATLTADTSSSTAYMQISSLTSEDSAVYFCARGD
SVPFAYWGQGTLVTVSAASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

By "huMy9-6" (also termed "Z4681A") is meant a humanized antibody or epitope binding fragment thereof that specifically binds leukocyte differentiation antigen CD33, such as human CD33. Exemplary sequences for the huMy9-6 heavy chain variable region portion are described in U.S. Patent Publication No. 20060177455, which is incorporated herein by reference in its entirety. Exemplary sequences for the huMy9-6 light chain variable region portion are known in the art and described in U.S. Pat. Nos. 7,557,189, 7,342,110, 8,119,787 and 8,337,855, which are incorporated herein by reference in their entireties. An exemplary huMy9-6 antibody of the invention may include or consists of the following CDRs (shown in bold and underline) or the following light chain (LC) and heavy chain (HC) sequences:

huMy9-6 LC (SEQ ID NO: 8)
EIVLTQSPGSLAVSPGERVTMSCKSSQSVFFSSSQKNYLAWYQQIPGQSP
RLLIYWASTRESGVPDRFTGSGSGTDFTLTISSVQPEDLAIYYCHQYLSS
RTFGQGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC huMy9-6 HC (SEQ ID NO: 9)
QVQLQQPGAEVVKPGASVKMSCKASGYTFTSYYIHWIKQTPGQGLEWVGV
IYPGNDDISYNQKFQGKATLTADKSSTTAYMQLSSLTSEDSAVYYCAREV
RLRYFDVWGQGTTVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVY
TLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG

By "huMy9-6-sulfo-SPDB-DGN462" (also termed "IMGN779") is meant an anti-huCD33 antibody conjugated to an indolinobenzodiazepine dimer containing a monoimine moiety termed DGN462 via a cleavable disulfide linker.

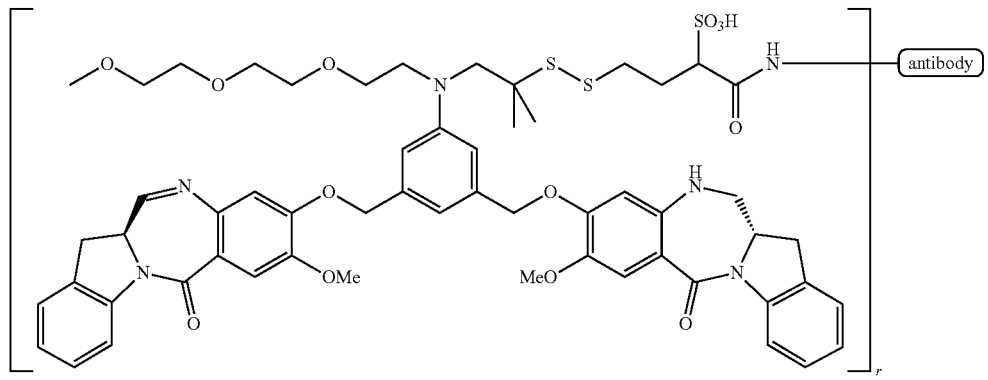

By "huEGFR-7R" (also termed "J2898A") is meant a humanized antibody or epitope binding fragment thereof that specifically binds EGFR, such as human EGFR. An exemplary huEGFR-7R antibody of the invention may include or consists of the following CDRs (shown in bold and underline) or the following light chain (LC) and heavy chain (HC) sequences:

huEGFR-7R LC v1.0
(SEQ ID NO: 10)
DIQMTQSPSSLSASVGDRVTITCRASQDINNYLAWYQHKPGKGPKLLIHY

TSTLHPGIPSRFSGSGRDYSFSISSLEPEDIATYYCLQYDNLLYTFGQ

GTLKLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC huEGFR-7R LC v1.01

DIQMTQSPSSLSASVGDRVTITCKASQDINNYLAWYQHKPGKGPKLLIHY
(SEQ ID NO: 11)
TSTLHPGIPSRFSGSGRDYSFSISSLEPEDIATYYCLQYDNLLYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC huEGFR-7R HC
(SEQ ID NO: 12)
QVQLVQSGAEVAKPGASVKLSCKASGYTFTSYWMQWVKQRPGQGLECIGT

IYPGDGDTTYTQKFQGKATLTADKSSSTAYMQLSSLRSEDSAVYYCARYD

APGYAMDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHANKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

By "huEGFR-7R-SMCC-DM1" (also termed "IMGN289") is meant an antibody drug conjugate that comprises an huEGFR-7R antibody, which specifically binds EGFR, conjugated to the maytansinoid N(2')-deacetyl-N(2')-(3-mercapto-1-oxopropyl)-maytansine (DM1) via the linker N-succinimidyl 4-(maleimidomethyl) cyclohexanecarboxy late (SMCC). The ADC huEGFR-7R-SMCC-DM1 is described, for example, in U.S. Pat. No. 8,790,649 and International Pat. Appl. Publication No. WO2012/058588, which are incorporated herein by reference in their entireties.

By "huCD37-3" is meant a humanized antibody or epitope binding fragment thereof that specifically binds CD37, such as human CD37. Exemplary sequences for huCD37-3 are described in U.S. Pat. No. 8,765,917 and International Pat. Appl. Publication No. WO2011/112978, which are incorporated herein by reference in their entireties. An exemplary huCD37-3 antibody of the invention may include or consists of the following CDRs (shown in bold and underline) or the following light chain (LC) and heavy chain (HC) sequences:

huCD37-3 LC
(SEQ ID NO: 13)
DIQMTQSPSSLSVSVGERVTITCRASENIRSNLAWYQQKPGKSPKLLVNV

ATNLADGVPSRFSGSGSGTDYSLKINSLQPEDFGTYYCQHYWGTTWTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC huCD37-3 HC v1.0
(SEQ ID NO: 14)
QVQVQESGPGLVAPSQTLSITCTVSGFSLTTSGVSWVRQPPGKGLEWLGV

IWGDGSTNYHPSLKSRLSIKKDHSKSQVFLKLNSLTAADTATYYCAKGGY

SLAHWGQGTLVTVSSASTKGPSVFPLAPSSKSTSGGTAALGCLVKDYFPE

PTVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTY

RVVSVLTVLHQDWLNGKEYKCKVSNKALPAPIEKTISAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG huCD37-3 HC v1.1

(SEQ ID NO: 15)
QVQVQESGPGLVAPSQTLSITCTVSGFSLTTSGVSWVRQPPGKGLEWLG<u>V</u>

<u>IWGDGSTN</u>YHSSLKSRLSIKKDHSKSQVFLKLNSLTAADTATYYCAKGGY

SLAHWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG

By "huCD37-3-SMCC-DM1" (also termed "IMGN529") is meant an antibody drug conjugate that comprises a humanized IgG1 antibody K7153A that specifically binds CD37 that is covalently linked via the uncleavable, maleimide-derived thioether-based linker succinimidyl 4-[N-maleimidomethyl]cyclohexane-1-carboxylate (SMCC) to the maytansinoid N(2')-deacetyl-N(2')-(3-mercapto-1-oxopropyl)-maytansine (DM1).

By "huCD37-50" is meant a humanized antibody or epitope binding fragment thereof that specifically binds CD37, such as human CD37. Exemplary sequences for huCD37-50 are described in U.S. Pat. No. 8,765,917 and International Pat. Appl. Publication No. WO2011/112978, which are incorporated herein by reference in their entireties. An exemplary huCD37-50 antibody of the invention may include or consists of the following CDRs (shown in bold and underline) or the following light chain (LC) and heavy chain (HC) sequences:

huCD37-50 LC (SEQ ID NO: 16)
EIVLTQSPATMSASPGERVTMTCSATSSVTYMHWYQQKPGQSPKRWIY<u>DT</u>

<u>SNLPY</u>GVPARFSGSGSGTSYSLTISSMEAEDAATYYCQQWSDNPPTFGQG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC huCD37-50 HC (SEQ ID NO: 17)
QVQLQESGPGLLKPSQSLSLTCTVSGYSITSGFAWHWIRQHPGNKLEWMG

<u>YILYSGSTV</u>YSPSLKSRISITRDTSKNHFFLQLNSVTAADTATYYCARGY

YGYGAWFAYWGQGTLVTVSAASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVGSCSVMHEALHNHYTQKSLSLSPG

By "huAnti-CD123" is meant a humanized antibody or epitope binding fragment thereof that specifically binds CD123, such as human CD123. Exemplary huAnti-CD123 antibodies are described in U.S. Provisional Appl. Ser. No. 62/186,161, which is incorporated herein by reference in its entirety.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, epitope binding antibody fragments (such as Fab, Fab', F(ab')2, and Fv fragments), single chain Fv (scFv) mutants, immunoglobulin new antigen receptor antibodies (IgNARs), which comprise single variable new antigen receptor domain antibody fragments ($V_{NARS}$, or $V_{NAR}$ domains), unibodies, in which the hinge region has been removed, nanobodies, antibody fragments consisting of a single monomeric variable antibody domain (Ablynx), minibodies, which are engineered antibody fragments comprising an scFv linked to a CH domain (Hu et al., Cancer Res. 56:3055-3061, 1996), DuoBodies®, which are bispecific modified IgG1 antibodies that include (i) a stable hinge region that is non-permissive for Fab arm exchange in vivo and (ii) an IgG4-like CH3 domain modified to be permissive for Fab arm exchange in vivo. (See, for example, WO2008/119353 and WO2011/131746), multispecific antibodies, such as bispecific antibodies generated from at least two intact antibodies, probodies, which are recombinant, masked monoclonal antibodies that remain inert in healthy tissue, but are activated specifically in the disease microenvironment (e.g., cleavage by a protease enriched or specific in a disease microenvironment) (See Desnoyers et al., Sci Transl Med 5:207ra144, 2013), chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991. National Institutes of Health, Bethesda Md.)); and (2) an approach based on crystallographic studies of antigen-antibody complexes (Al-lazikani et al (1997) J. Molec. Biol. 273:927-948)). In addition, combinations of these two approaches are sometimes used in the art to determine CDRs.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

The terms "cancer" and "cancerous" refer to or describe the physiological condition in mammals in which a population of cells are characterized by unregulated cell growth. Cancer can include a hematological cancer or a solid tumor. More specifically, the cancer is leukemia (e.g., acute myeloid leukemia (AML) acute monocytic leukemia, promyelocytic leukemia, eosinophilic leukaemia, acute lymphoblastic leukemia (ALL) such as acute B lymphoblastic leukemia (B-ALL), chronic myelogenous leukemia (CML), chronic lymphocytic leukemia (CLL)) or lymphoma (e.g., non-Hodgkin lymphoma), myelodysplastic syndrome (MDS), melanoma, lung cancer (e.g., non-small cell lung cancer; NSCLC), ovarian cancer, endometrial cancer, peritoneal cancer, pancreatic cancer, breast cancer, prostate cancer, squamous cell carcinoma of the head and neck, and cervical cancer.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc.) with the desired specificity, affinity, and capability while the constant regions are homologous to the sequences in antibodies derived from another (usually human) to avoid eliciting an immune response in that species.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. Examples of diseases include neoplasias and cancers to be treated with a composition of the invention.

By "effective amount" is meant the amount of an agent required to ameliorate the symptoms of a disease relative to an untreated patient. The effective amount of active agent(s) (e.g., an antibody drug conjugate (ADC) or drug) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

By "formulate" is meant a process used to produce a drug product.

The term "humanized antibody" refers to forms of non-human (e.g. murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability (Jones et al., 1986, Nature, 321:522-525; Riechmann et al., 1988, Nature, 332:323-327; Verhoeyen et al., 1988, Science, 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

The goal of humanization is a reduction in the immunogenicity of a xenogenic antibody, such as a murine antibody, for introduction into a human, while maintaining the full antigen binding affinity and specificity of the antibody.

Humanized antibodies may be produced using several technologies, such as resurfacing and CDR grafting. As used herein, the resurfacing technology uses a combination of molecular modeling, statistical analysis and mutagenesis to alter the non-CDR surfaces of antibody variable regions to resemble the surfaces of known antibodies of the target host.

Strategies and methods for the resurfacing of antibodies, and other methods for reducing immunogenicity of antibodies within a different host, are disclosed in U.S. Pat. No. 5,639,641 (Pedersen et al.), which is hereby incorporated in its entirety by reference. Briefly, in a preferred method, (1) position alignments of a pool of antibody heavy and light chain variable regions are generated to give a set of heavy and light chain variable region framework surface exposed positions wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 angstroms of any atom of any residue of the complementarity-determining regions of the rodent antibody; and (5) the humanized rodent antibody having binding specificity is produced.

Antibodies can be humanized using a variety of other techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., 1991. Molecular Immunology 28(4/5):489-498; Studnicka G. M. et al., 1994, Protein Engineering 7(6):805-814; Roguska M. A. et al., 1994, PNAS 91:969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and International Pat. Appl. Publication Nos.: WO 98/46645, WO 98/50433, WO 98/24893, WO 98/16654, WO 96/34096, WO 96/33735, and WO 91/10741 (said references incorporated by reference in their entireties).

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "antibody drug conjugate" or "ADC" as used herein refers to a compound that is linked to a cell binding agent (i.e., an antibody or fragment thereof). Typically, the cell binding agent (e.g., antibody) is covalently bound to the drug by a linker.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

A "linker" is any chemical moiety that is capable of linking a compound to a protein. In one embodiment, a linker links a drug, such as a maytansinoid, to a cell-binding agent, such as an antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and known in the art.

Exemplary cleavable linkers include, but are not limited to: N-succinimidyl 3-(2-pyridyldithio) propionate (SPDP), N-succinimidyl 4-(2-pyridyldithio)butanoate (SPDB), N-succinimidyl 4-(2-pyridyldithio)2-sulfobutanoate (sulfo-SPDB), and disulfide N-succinimidyl 4-(2-pyridyldithio) pentanoate (SPP). Exemplary non-cleavable linkers include, but are not limited to: 2-iminothiolane, acetylsuccinic anhydride, and succinimidyl 4-[N-maleimidomethyl]cyclohexane-1-carboxylate (SMCC). The generic linkers 2-iminothiolane and acetylsuccinic anhydride can be used as cleavable or non-cleavable linkers.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

By "specifically binds" is meant a compound or antibody that recognizes and binds a polypeptide of interest, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of interest or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

The term "therapeutically effective amount" refers to an amount of an antibody or other drug effective to "treat" a disease or disorder in a subject or mammal. In the case of cancer, the therapeutically effective amount of the drug can reduce the number of cancer cells; reduce the tumor size; inhibit (i.e., slow to some extent or stop) cancer cell infiltration into peripheral organs; inhibit (i.e., slow to some extent or stop) tumor metastasis; inhibit, to some extent, tumor growth; and/or relieve to some extent one or more of the symptoms associated with the cancer. See the definition herein of "treating". To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value, Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 4 provides a scatter plot and a table that simulates the likely effect of drug-to-antibody ratio (DAR) and concentration on eye toxicity. The DARs were calculated and the corresponding ADCs were not actually administered to patients.

FIG. 5 includes two graphs showing the lack of effect of DAR on median tumor volume in KB and IGROV-1 murine xenograft models when the huMov19-sulfo-SPDB-DM4 conjugate is administered at the same DM4 dose. Mice were dosed with huMov19-sSPDB-DM4. All conjugates were dosed at 25 µg/kg of DM4 and variable antibody dose (higher for the low DAR conjugates and lower for the high DAR conjugates). Similar anti-tumor activity was observed regardless of variable DAR and antibody dose.

FIGS. 9A and 9B are tables showing the advantage of preparing an ADC composition based on DM4 concentration. FIG. 9A shows the allowable DM4 concentrations in μg/ml that results when an antibody drug conjugate is formulated at a target antibody concentration (5.0±1.0 mg/ml) and DAR 3.4±0.5 (circled). The DM4 concentration is 91.1 at the 5.0 mg/mL target antibody concentration and the 3.4 DAR target (box). Lower potency variation (boxed area of DM4 concentrations) allowed by formulating based on DM4 concentration with a ±10% specification. Target DAR, antibody and DM4 concentrations are boxed. In FIG. 9B, antibody concentration specification fails at the high-low DAR extremes (boxed areas). Target DAR, antibody and DM4 concentrations are boxed.

FIGS. 10A-10C are graphs showing the effect of formulating an antibody drug conjugate (ADC) batch by varying antibody concentration to achieve a target drug (DGN462) concentration. "USL" and "LSL" denote the upper and lower specification limits for antibody concentration. DGN462 is an exemplary drug. The vertical line (elongated "I") denotes the upper and lower limits of drug concentration. "DAR" denotes drug-to-antibody ratio.

DETAILED DESCRIPTION OF THE INVENTION

Figure 1:
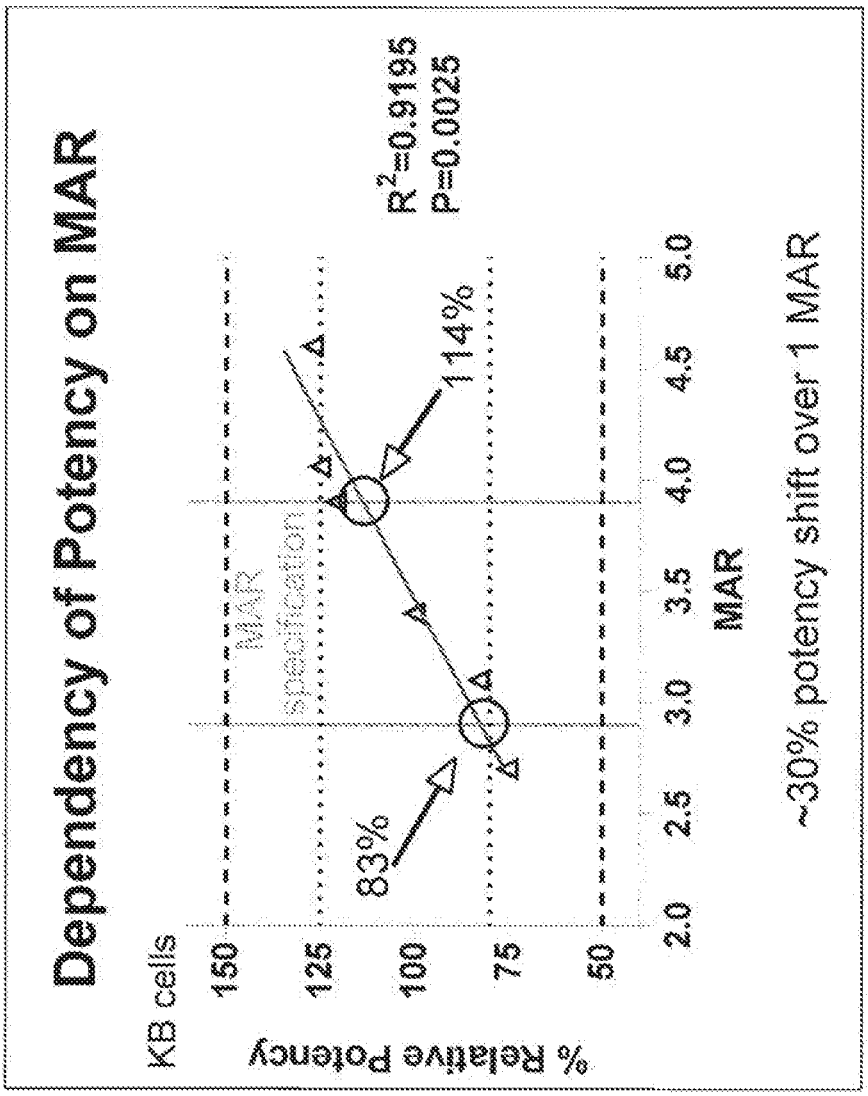
FIG. 1 is a graph that illustrates the dependence of cytotoxic potency on the maytansinoid-to-antibody ratio (MAR) for huMov19-sulfo-SPDB-DM4, which is an immunoconjugate that includes a humanized monoclonal antibody (huMov19) against FOLR1 conjugated to the cytotoxic maytansinoid DM4 through a sulfo-SPDB linker. Cytotoxic potency is measured relative to an huMov19-sulfo-SPDB-DM4 reference standard having a MAR of 3.4, Percent potency=$EC_{50}$ reference/$EC_{50}$ test article*100%.

The invention provides improved methods for formulating a therapeutic composition comprising an antibody drug conjugate ("ADC"), thereby narrowing variability in potency between batches of ADC and/or narrowing drug and antibody specifications over a broader drug- to antibody ratio (DAR) range.

In one aspect, the invention is based, at least in part, on the discovery that the efficacy and toxicity of some ADCs is driven entirely or in part by the dose of drug administered rather than the dose of antibody. Formulating ADC compositions based on a target drug concentration advantageously minimizes potency variations in the finished drug product and ensures that patients are dosed within a narrow intended range.

Conventionally, antibody drug conjugate therapeutic compositions have been formulated based on antibody concentration. Some variability is inherent in formulating antibody drug conjugates based on antibody concentration, even when remaining within the allowable ranges of a given specification. In particular, at the end of the ADC manufacturing process, the concentration of antibody in the conjugate is measured, and the conjugate is diluted to reach the target drug concentration based on the fixed antibody concentration. In practice, the antibody concentration in the finished drug product is allowed to vary from the target concentration. In one example, the formulation specification allows ±20% variation in antibody-based concentration (e.g., 4.0-6.0 mg/mL allowed for a target antibody concentration of 5.0 mg/mL). Thus, depending on the DAR, the ADC potency in the finished drug product could vary by as much as ±35% and potentially fall outside the desired range.

The formulation methods reported herein below involve determining drug concentration at a fixed antibody concentration and fixed drug-to-antibody ratio and formulating the antibody drug conjugate composition to achieve a desired drug concentration. In brief, formulating the ADC composition based on drug concentration and adding a drug concentration specification of, for example ±10% significantly narrows the potency present in the finished drug product to ±10% of the target drug concentration (±10% specification). By formulating the ADC based on drug concentration and allowing no more than 10% variation in drug concentration, potency is permitted to vary by only ±10%. Thus, the new formulation methods of the present invention eliminate DAR potency dependence by formulating to a narrow range of drug concentration. This formulation strategy only slightly increases the risk that antibody concentration will be outside specification, and thus the risk of batches failing to conform to specification is fairly low. Such improved formulation methods ensure that patients are dosed within a narrow intended range without adding substantially to the risk that a batch of ADC will fail to conform to specification.

In yet another aspect, the invention provides a method of reducing potency variability in a composition comprising an antibody drug conjugate. The method involves formulating the antibody drug conjugate by targeting a variable concentration of both the drug and the antibody (i.e. by having small variations (±4-9%) in both concentration values rather than large changes in one concentration (±10-15%) within a range where both specifications overlap, thereby reducing potency variability in the composition. In one embodiment, a small variation is about 4, 5, 6, 7, 8, or 9%. In other embodiments, a large change is about 10, 11, 12, 13, 14, or 15%.

In another aspect, the invention provides a method of reducing potency variability in a composition comprising an antibody drug conjugate. The method involves formulating the antibody drug conjugate by targeting a variable concentration of either the drug or the antibody within a range where both specifications overlap, thereby reducing potency variability in the composition.

Antibody Drug Conjugate Formulation

ADC cancer therapeutics are formulated similarly to antibody cancer therapeutics; that is, based on the antibody protein concentration. While the drug product label gives information about the "nominal" or target concentration, which is the basis for dosing (for instance on a mg/kg or mg/m$^2$ basis), a typical specification for antibody concentration is target ±10-20%. Potency of ADCs is generally linear relative to concentration, therefore the potency of a drug product may vary by ±20%. ADCs, unlike antibodies, have an additional potential for variable potency due to the Drug to Antibody Ratio (DAR). Typical DAR specifications for early clinical development are target ±15%, which would allow the amount of linked cytotoxic to vary for a given concentration of antibody. For most ADCs it can be demonstrated that there is a linear relationship between the DAR and potency indicating that the potency is in part, or entirely, dictated by the concentration of conjugated drug administered.

For many ADCs it can be demonstrated in rodents that the toxicity is entirely dependent on the dose of conjugated drug administered regardless of the dose of antibody. Thus, the toxicity is independent of DAR as long as the administered dose of the conjugated drug is the same. For some ADCs, where the antibody has no inherent anti-tumor activity, efficacy depends entirely on the dose of drug. In such cases, the efficacy is the same regardless of DAR as long as the administered dose of the conjugated drug is the same. However, a typical specification for antibody concentration and DAR allows the concentration of the conjugated drug to vary somewhat. For some ADCs, even where the antibody has inherent anti-tumor activity or is, for example considered a functional antibody, the ADCs efficacy may still be driven more by the dose of drug rather than by the antibody.

In cases where it can be demonstrated that the efficacy and toxicity of the ADC are driven primarily by the amount of conjugated drug administered, narrowing the specification features the use of the methods described herein for formulating huMy9-6-sulfo-SPDB-DGN462, which is an antibody drug conjugate comprising DGN462 conjugated to the anti-CD33 antibody, huMy9-6, via a cleavable disulfide linker, s-SPDB. Other drugs useful in the invention include benzodiazepines such as those represented in Table 1 or variations thereof, and by the following structural formulas:

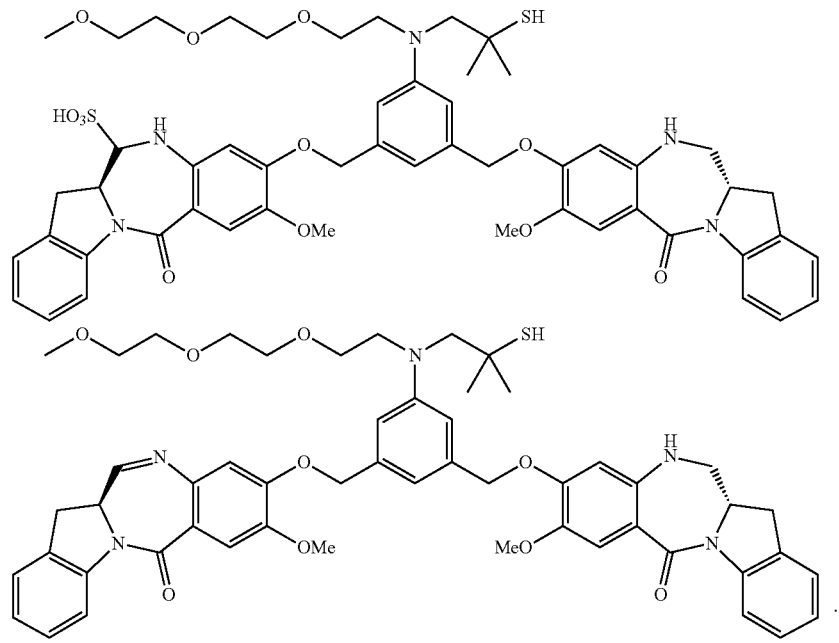

for the concentration of conjugated drug rather than antibody can prove beneficial. Accordingly, the invention provides methods for formulating a therapeutic composition based on the concentration of the drug rather than the concentration of the antibody. The target concentration for the drug would be the calculated drug concentration at a fixed antibody concentration and fixed DAR. A specification set close to the target conjugated drug concentration would dictate the allowable potency variation in the drug product vial. Therefore, a specification for drug concentration of ±10% would narrow the allowable potency variation to ±10%.

In other embodiments, a therapeutic composition may be formulated by targeting a variable drug concentration based on the DAR and antibody specification to achieve an ADC therapeutic composition that falls within the center of the effective specification range for antibody and the drug concentrations, where both the drug and antibody concentrations overlap. At DARs of within ±5% of target the center of effective range achieved by targeting a variable drug concentration may be substantially similar to the final formulated product, if a static drug concentration is used. Improvements are realized when DAR varies between ±5-15% of target DAR. At these upper and lower DAR limits, formulating a therapeutic composition by targeting a variable drug concentration can provide smaller variability with respect to both drug (e.g., about ±4%) and antibody concentration (e.g., about ±10%) versus targeting a static drug concentration, which would vary the antibody concentration by about ±15%. Such ranges are useful in formulating ADC compositions, examples of which includes huMy9-6-sulfo-SPDB-DGN462. In one embodiment, the invention Antibody Drug Conjugates The present invention is directed to improved methods for formulating an ADC, comprising an antibody (e.g., antibody that binds a tumor antigen) or antibody fragment, and their functional equivalents as disclosed herein, linked or conjugated to a cytotoxic agent (e.g., drug or prodrug). A variety of antibodies can be used in the methods of the invention. In particular embodiments, the antibody specifically binds an antigen or ligand such as FOLR1 (also known as FRα), CD33, CD123, CD19, MUC1, CA6, CD37, EGFR, and fragments of any of the above-listed polypeptides. In particular embodiments, the invention includes, but is not limited to, an ADC that includes any of the following antibodies: huMov19, huMy9-6, huAnti-CD123, huB4, huDS6, huCD37-50, huCD37-3, and huEGFR-7R.

Suitable drugs or prodrugs are known in the art. The drugs or prodrugs can be cytotoxic. A cytotoxic drug used in the ADCs of the present invention may be any compound that results in the death of a cell (e.g., cancer cell), or induces cell death, or in some manner decreases cell viability, and includes, for example, tubulin inhibitors. DNA damaging agents, DNA cross linkers, DNA alkylating agents, and cell cycle disrupters. In particular embodiments, suitable cytotoxic drugs include maytansinoids and maytansinoid analogs. Other suitable cytotoxic drugs include, for example, benzodiazepines (e.g., pyrrolobenzodiazepines and indolinobenzodiazepines; see also Table 1: compounds D1-D10 and DGN462), taxoids, CC-1065 and CC-1065 analogs, duocarmycins and duocarmycin analogs, enediynes, such as calicheamicins, dolastatin and dolastatin analogs including auristatins, tomaymycin derivatives, leptomycin derivatives, methotrexate, cisplatin, carboplatin, daunorubicin, doxorubicin, vincristine, vinblastine, melphalan, mitomycin C, chlorambucil, and morpholino-doxorubicin.

ADCs can be prepared by using a linking group in order to link a drug or prodrug to the antibody or functional equivalent. Suitable linking groups are well known in the art and include, for example, disulfide groups, thioether groups, acid labile groups, photolabile groups, peptidase labile groups and esterase labile groups.

The drug or prodrug may, for example, be linked to the antibody or fragment thereof through a disulfide bond. The linker molecule or crosslinking agent can include a reactive chemical group that can react with the antibody or fragment thereof. The reactive chemical groups for reaction with the cell-binding agent can be, for example, N-succinimidyl esters and N-sulfosuccinimidyl esters. Additionally, the linker molecule comprises a reactive chemical group, such as a dithiopyridyl group that reacts with the drug to form a disulfide bond. Linker molecules include, for example, N-succinimidyl 3-(2-pyridyldithio) propionate (SPDP) (see, e.g., Carlsson et al., Biochem. J., 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)2-sulfobutanoate (sulfo-SPDB) (see US Publication No. 20090274713), N-succinimidyl 4-(2-pyridyldithio)pentanoate (SPP) (see, e.g., CAS Registry number 341498-08-6), 2-iminothiolane, or acetylsuccinic anhydride, succinimidyl 4-[N-maleimidomethyl]cyclohexane-1-carboxylate (SMCC). For example, the antibody or cell binding agent can be modified with crosslinking reagents and the antibody or cell binding agent containing free or protected thiol groups thus derived is then reacted with a disulfide- or thiol-containing maytansinoid to produce conjugates. The conjugates can be purified by chromatography, including but not limited to HPLC, size-exclusion, adsorption, ion exchange and affinity capture, dialysis or tangential flow filtration.

In one aspect of the present invention, an antibody is linked to cytotoxic drugs via disulfide bonds and a polyethylene glycol spacer in enhancing the potency, solubility or the efficacy of the ADC. Such cleavable hydrophilic linkers are described, for example, in WO2009/0134976. The additional benefit of this linker design is the desired high monomer ratio and the minimal aggregation of the antibody-drug conjugate. Specifically contemplated in this aspect are conjugates of cell-binding agents and drugs linked via disulfide group (—S—S—) bearing polyethylene glycol spacers ((CH$_2$CH$_2$O)$_{n=1-14}$) with a narrow range of drug load of 2-8 are described that show relatively high potent biological activity toward cancer cells and have the desired biochemical properties of high conjugation yield and high monomer ratio with minimal protein aggregation.

Many of the linkers disclosed herein are described in detail in U.S. Pat. Nos. 7,989,598; 8,163,888; 8,198,417; 8,236,319; 8,563,509; U.S. Patent Publication No.: US20130029900 and International Pat. Appl. Publication Nos. WO2009/0134976; WO2009/134977; and WO2012/177837; the contents of each of the aforementioned patents and applications are entirely incorporated herein by reference.

The present invention includes aspects wherein about 2 to about 8 drug molecules, for example, maytansinoids, benzodiazepine compounds, auristatins, DNA alkylators, or other compounds of interest, are linked to an antibody or fragment thereof, the anti-tumor effect of the conjugate is much more efficacious as compared to a drug load of a lesser or higher number of drugs linked to the same cell binding agent.

In one aspect, the drug to antibody ratio averages from about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1). Virtually any cytotoxic drug can be used in an ADC. In certain embodiments, cytotoxic agents useful in the present invention are maytansinoids and maytansinoid analogs. Examples of suitable maytansinoids include esters of maytansinol and maytansinol analogs. Included are any drugs that inhibit microtubule formation and that are highly toxic to mammalian cells, as are maytansinol and maytansinol analogs.

In particular embodiments, an ADC of the invention comprises a maytansinoid. Maytansinoids useful in the invention include, but are not limited to, N$^{2'}$-deacetyl-N*-(3-mercapto-1-oxopropyl)-maytansine (DM1), N$^{2'}$-deacetyl-N$^{2'}$ (4-mercapto-1-oxopentyl)-maytansine (termed DM3), and N$^{2'}$-deacetyl-N$^{2'}$-(4-mercapto-4-methyl-1-oxopentyl) maytansine (DM4).

DM1 is represented by the following structural formula:

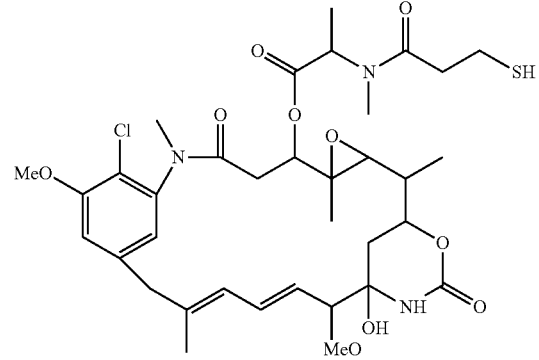 [SMILES: COc1cc2cc(c1Cl)N(C)C(=O)CC(OC(=O)C(C)N(C)C(=O)CCS)C1(C)OC1C(C)C1CC(O)(NC(=O)O1)C(OC)/C=C/C=C(\C)C2]

See, also U.S. Patent Publication No. 20130156796.

DM4 is represented by the following structural formula:

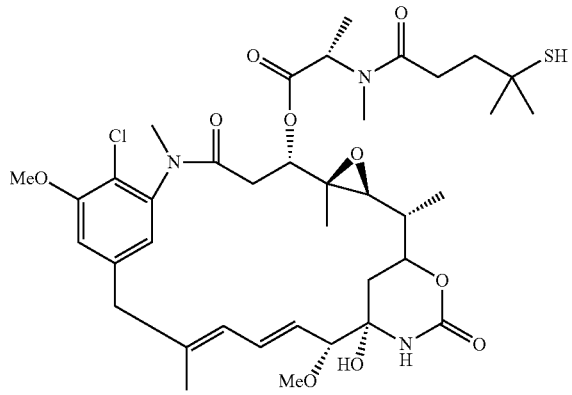 [SMILES: COc1cc2cc(c1Cl)N(C)C(=O)C[C@H](OC(=O)[C@H](C)N(C)C(=O)CCC(C)(C)S)[C@]1(C)O[C@H]1[C@H](C)C1C[C@@](O)(NC(=O)O1)[C@H](OC)/C=C/C=C(\C)C2]

See, also U.S. Patent Publication No. 20130156796.

Examples of suitable maytansinol esters include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 7,276,497 and 7,473,796.

Another maytansinoid comprising a side chain that contains a sterically hindered thiol bond is $N^{2'}$-deacetyl-$N^{2'}$ (4-mercapto-1-oxopentyl)-maytansine (termed DM3), represented by the following structural formula (V):

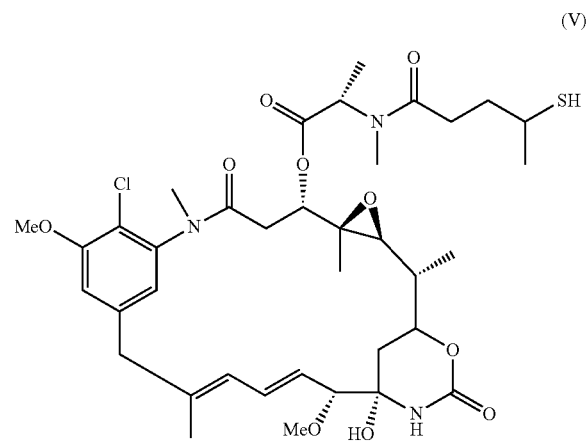 [SMILES: COc1cc2cc(c1Cl)N(C)C(=O)C[C@H](OC(=O)[C@H](C)N(C)C(=O)CCC(C)S)[C@]1(C)O[C@H]1[C@H](C)C1C[C@@](O)(NC(=O)O1)[C@H](OC)/C=C/C=C(\C)C2]

(V)

Each of the maytansinoids taught in U.S. Pat. Nos. 5,208,020 and 7,276,497, can also be used in the conjugate of the present invention. In this regard, the entire disclosure of U.S. Pat. No. 5,208,020 and U.S. Pat. No. 7,276,697 is incorporated herein by reference. The carbon positions of an exemplary maytansinoid structure are provided below:

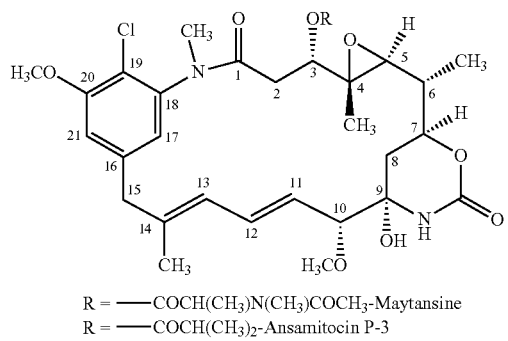

R = —COCH(CH$_3$)N(CH$_3$)COCH$_3$-Maytansine
R = —COCH(CH$_3$)$_2$-Ansamitocin P-3

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to chemically link the linking moiety, and in some particular embodiments, the C-3 position of maytansinol serves as the position to chemically link the linking moiety.

Several descriptions for producing such antibody-maytansinoid conjugates are provided in U.S. Pat. Nos. 6,333, 410, 6,441,163, 6,716,821, and 7,368,565, each of which is incorporated herein in its entirety.

In general, a solution of an antibody in aqueous buffer can be incubated with a molar excess of maytansinoids having a disulfide moiety that bears a reactive group. The reaction mixture can be quenched by addition of excess amine (such as ethanolamine, taurine, etc.). The maytansinoid-antibody conjugate can then be purified by gel filtration.

The average number of maytansinoid molecules bound per antibody molecule can be determined by measuring spectrophotometrically the absorbance at 252 nm and 280 nm and determining the molar concentration of the antibody and the molar concentration of the drug An exemplary calculation is shown herein below for huMov19-sulfo-SPDB-DM4. The average number of maytansinoid molecules per antibody is then calculated by dividing the molar concentration of the drug by the molar concentration of the antibody. The average number of maytansinoid molecules/antibody can be, for example, 1-10 or 2-5. In some embodiments, the average number of maytansinoid molecules/antibody is 3.4.

In particular embodiments, an ADC of the invention comprises a benzodiazepine. Benzodiazepines useful in the invention include, for example, pyrrolobenzodiazepines and indolinobenzodiazepines (see also Table 1: compounds D1-D10 and DGN462). In various embodiments of the previous aspects, the benzodiazepine compounds are selected from the representative cytotoxic agents D1-D10 and DGN462 listed in Table 1. DGN462 is described, for example, in U.S. Pat. No. 8,765,740, which is incorporated herein by reference in its entirety. Compound D1 is described, for example, in U.S. Provisional Appl. Ser. No. 62/045,236 and "Antibody-Drug Conjugates (ADCs) of Indolino-Benzodiazepine DNA-Alkylating Agents". 2015 AACR, Abstract number 652. Compound D2 is described, for example, in U.S. Provisional Appl. Ser. No. 62/045,248 and "Antibody-Drug Conjugates (ADCs) of Indolino-Benzodiazepine DNA-Alkylating Agents", 2015 AACR, Abstract number 652.

Pharmaceutical Compositions

The present invention further provides pharmaceutical compositions comprising one or more of the ADCs described herein. In certain embodiments, the pharmaceutical compositions further comprise a pharmaceutically acceptable vehicle. These pharmaceutical compositions find use in inhibiting tumor growth and treating cancer in human patients.

Exemplary antibody drug conjugates used in the pharmaceutical compositions of the invention, include, without limitation: huMov19-sulfo-SPDB-DM4, huMov19-sulfo-SPDB-D1, huMov19-D2, huMov19-sulfo-SPDB-D10, huMov19-sulfo-SPDB-DGN462, huMy9-6-sulfo-SPDB-D1, huMy9-6-D2, huMy9-6-sulfo-SPDB-D10, huMy9-6-sulfo-SPDB-DGN462, huAnti-CD 123-sulfo-SPDB-D1, huAnti-CD123-D2, huAnti-CD123-sulfo-SPDB-D10, huAnti-CD123-sulfo-SPDB-DGN462, huB4-SPDB-DM4, huDS6-SPDB-DM4, huCD37-3-SMCC-DM1, huCD37-50-SMCC-DM1, or huEGFR-7R-SMCC-DM1.

In certain embodiments, formulations are prepared for storage and use by combining a purified ADC of the present invention with a pharmaceutically acceptable vehicle (e.g. carrier, excipient) (Remington, The Science and Practice of Pharmacy 20th Edition Mack Publishing, 2000). The invention provides for the formulation of such compositions based on drug concentration. In some embodiments, an ADC of the invention is provided in a suitable carrier, diluent and/or excipient, such as 0.9% saline (0.9% w/v NaCl), 5% (w/v) dextrose; and may also contain a stabilizing agent such as Tween 20. In particular embodiments, the ADC is provided in an IV bag or in a drug vial.

Other suitable pharmaceutically acceptable vehicles include, but are not limited to, nontoxic buffers, such as phosphate, citrate, acetate, succinate and other organic acids; salts such as sodium chloride antioxidants including ascorbic acid and methionine; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol.

The pharmaceutical compositions of the present invention can be administered in any number of ways for either local or systemic treatment. Administration can be parenteral including intravenous, intra-arterial, or infusion; oral; transdermal; or intracranial (e.g., intrathecal or intraventricular) administration.

Kits Comprising Antibody Drug Conjugates

The present invention provides kits that comprise antibody drug conjugates (ADC) that can be used to perform the methods described herein. In certain embodiments, a kit comprises an ADC in one or more containers, where the amount of ADC is based on the drug concentration and where the amount of ADC varies by no more than ±10% from specification. One skilled in the art will readily recognize that the disclosed ADCs can be readily incorporated into one of the established kit formats that are well known in the art. If desired, the kit may include instructions for use of the ADC for patient therapy. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: ADC In Vitro Potency Depends on the Amount of Drug Delivered to a Cell or Subject The anti-FOLR1 monoclonal antibody moiety of huMov19-sulfo-SPDB-DM4 targets and binds to the cell surface antigen FOLR1 (also known as FRα). After antibody-antigen interaction and internalization, the immunoconjugate releases DM4, which binds to tubulin and disrupts microtubule assembly/disassembly dynamics, thereby inhibiting cell division and cell growth of FOLR1-expressing tumor cells, FOLR1, a member of the folate receptor family is overexpressed on a variety of epithelial-derived cancer cells.

Figure 2:
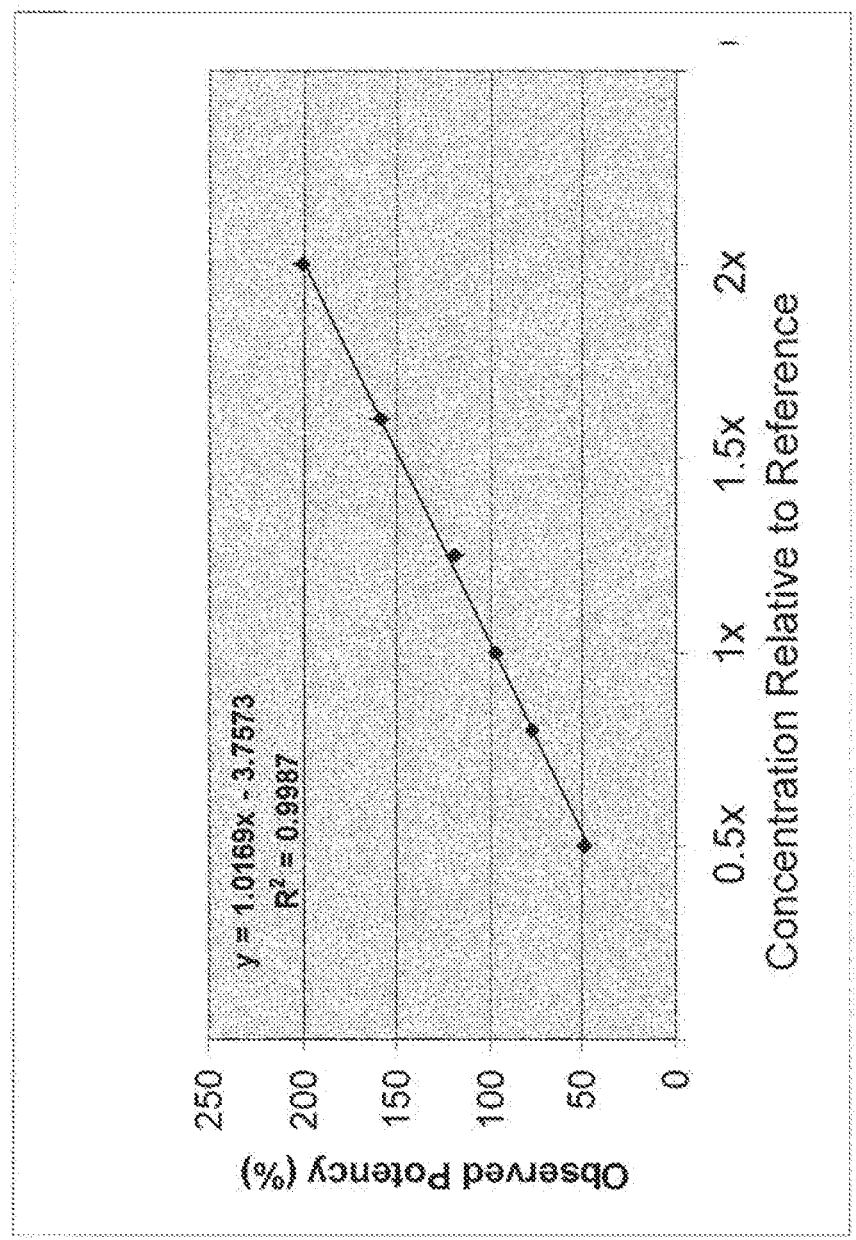
FIG. 2 is a graph showing the dependence of cytotoxic potency on the concentration of huMov19-sulfo-SPDB-DM4.

The in vitro potency of an antibody drug conjugate (ADC) is linearly related to drug antibody ratio (DAR), also termed maytansinoid-to-antibody ratio (MAR) (FIG. 1). The data shown in FIGS. 1 and 2 were generated using huMov19-sulfo-SPDB-DM4 as an exemplary ADC. In fact, there was a thirty-one percent potency shift over one DAR (i.e., 2.9-3.9) resulting from a calculated 29% difference in the dose of DM4. FIG. 2 shows a general dependence of cytotoxic potency on huMov19-sulfo-SPDB-DM4 concentration. When the conjugate concentration is diluted to half the concentration of the reference standard, the cytotoxic potency is half that of the reference standard. Likewise when the starting concentration of the conjugate is double that of the reference standard, the cytotoxic potency is double relative to the reference standard. Details of the Specific Cytotoxicity Assay are provided herein below in Example 6.

Figure 3:
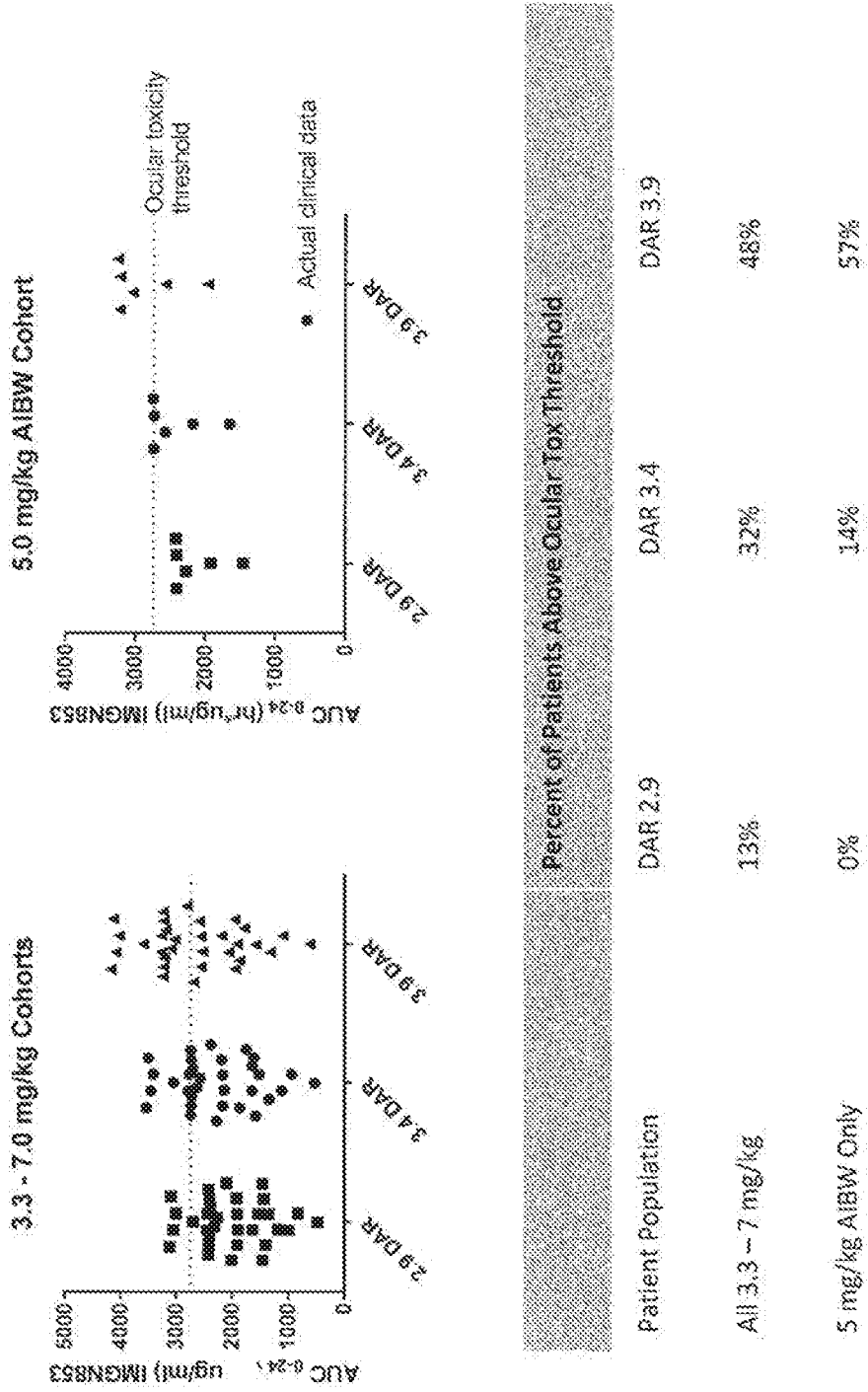
FIG. 3 provides two scatter plots and a table that simulate the likely effect of drug-to-antibody ratio (DAR) on eye toxicity ("ocular tox"). AIBW refers to Adjusted Ideal Body Weight. The DARs were calculated based on drug dosing levels.

At a target DAR of 3.4, acceptable variability ranges allow for the actual DAR present in the finished drug product, to vary between 2.9 and 3.9 (FIG. 3).

Example 2: DM4 Dose Drives In Vivo Toxicity and Efficacy

For huMov19-sulfo-SPDB-DM4, it is desirable to achieve as high an ADC level as possible to achieve efficacy without approaching the ocular toxicity threshold. As shown in FIG. 3, when huMov19-sulfo-SPDB-DM4 DAR is approximately 3.4, and dosage ranges between 3.3 and 7 mg/kg, 32% of patients were found to be above the ocular toxicity level. When huMov19-sulfo-SPDB-DM4 DAR is 2.9, and dosage ranges between 3.3 and 7 mg/kg, 13% of patients would be expected to be above the ocular toxicity level. When huMov19-sulfo-SPDB-DM4 DAR is 3.4, and dosage ranges between 3.3 and 7 mg/kg, 32% of patients are expected to be above the ocular toxicity level based on the decreased DM4 dose they would receive. When huMov19-sulfo-SPDB-DM4 DAR is 3.9, and dosage ranges between 3.3 and 7 mg/kg, 48% of patients are expected to be above the ocular toxicity level based on the increased DM4 dose they would receive.

At 5 mg/kg huMov19-sulfo-SPDB-DM4 (Adjusted Ideal Body Weight) where DAR is 2.9, none of the patients exceeded the ocular toxicity threshold. However, where DAR is 3.4 or 3.9 at 5 mg/kg huMov19-sulfo-SPDB-DM4, 14% and 57% of patients, respectively, exceeded the ocular toxicity threshold. Actual clinical data is shown for the 3.4 DAR cohort in FIG. 4 (closed circles on graph). The remaining data reflects a simulated dosage analysis.

FIG. 4 demonstrates the importance of ensuring that patients receive a dose within a narrow intended range. Ideally, to ensure maximum efficacy and safety, patients would receive a dose of huMov19-sulfo-SPDB-DM4 that approaches, but that does not exceed, the ocular toxicity threshold.

As discussed in Examples 3 and 4, for huMov19-sulfo-SPDB-DM4, toxicity depends on the amount of DM4 administered. Preclinical efficacy studies with huMov19-sulfo-SPDB-DM4 showed that there is no DAR dependency when DM4 dose is the same. Moreover, preclinical toxicity studies with huMov19-sulfo-SPDB-DM4 and many other conjugates showed that toxicity is driven by linked DM4 dose regardless of DAR.

Example 3: Anti-Tumor Activity of huMov19-Sulfo-SPDB-DM4 was Independent of DAR

In vivo studies analyzing huMov19-sulfo-SPDB-DM4 activity (FIG. 5) in KB and IGROV-1 murine xenograft models were carried out. The KB cell line was established from a HeLa cell contamination of a tumor cell. It is used as a tumor model because it forms a tumor in nude mice with reproducible characteristics and over expresses the folate receptor. The IGROV-1 tumor model is derived from a human ovarian carcinoma.

HuMov19-sulfo-SPDB-DM4 with different DARs, ranging from 2.5 to 4.1, were administered to mice bearing KB or IGROV-1 tumor xenografts, at a DM4 dose of 25 µg/kg and variable antibody dosages. As shown in FIG. 5, as long as the same DM4 dose was administered, the DAR did not impact efficacy. The results of this analysis indicated that DM4 dosage determined efficacy in FOLR1-positive KB and IGROV-1 tumor models, regardless of the DAR.

Example 4: Toxicity was independent of drug antibody ratio

Figure 6:
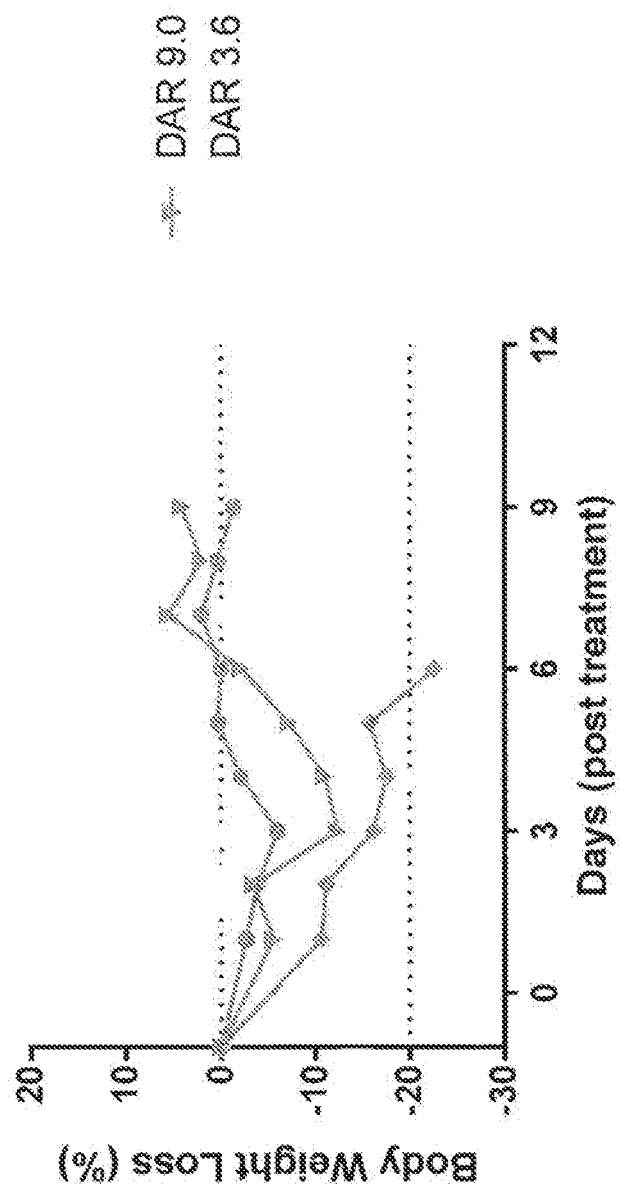
FIG. 6 is a graph showing the similar effect of DM4 dose on murine body weight for a conjugate having 9.0 DAR compared with 3.6 DAR when the administered DM4 dose is the same. All conjugates were dosed at 1.4 mg/kg of DM4 and variable antibody dose (higher for the low DAR conjugates and lower for the high DAR conjugates).

An in vivo study was undertaken to assess the impact of the drug antibody ratio on maximum tolerated dose (MTD) of huMov19-sulfo-SPDB-DM4 (FIG. 6). Mice received huMov19-sulfo-SPDB-DM4 at a fixed DM4 dose of 1400 µg/kg, where the antibody dose varied. Murine body weight was monitored as a measure of toxicity. The ADC's administered varied widely in drug to antibody ratio (e.g., DAR 9.0 vs. DAR 3.6). Interestingly, as long as the same DM4 dosage was administered, the DAR did not affect toxicity within the 3.6-9.0 range, Thus, toxicity was independent of DAR.

Figure 7:
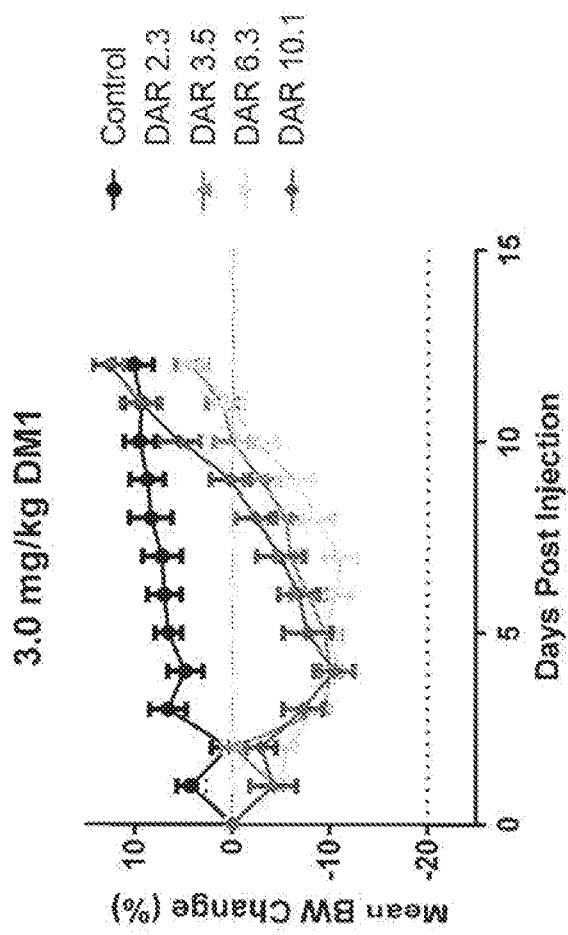
FIG. 7 is a graph showing the similar effect of DM1 dose on mean body weight change for conjugates having various maytansinoid-to-antibody ratios when the administered DM1 dose is the same. All conjugates were dosed at 3.0 mg/kg of DM1 and variable antibody dose (higher for the low DAR conjugates and lower for the high DAR conjugates). Toxicity was similar for all conjugates regardless of DAR.

In another in vivo toxicity analysis, the ADC huEGFR-7R-SMCC-DM1 was administered at a fixed DM1 dose of 3.0 mg/kg. The DAR varied (e.g., 2.3, 3.5, 6.3, 10.1), but DM1 dosage was held constant. Mean body weight (BW) change was monitored as an indicator of toxicity. The body weight loss was similar for the different DAR conjugates indicating that toxicity was independent of DAR as long as the DM1 dose was held constant (FIG. 7).

Figure 8:
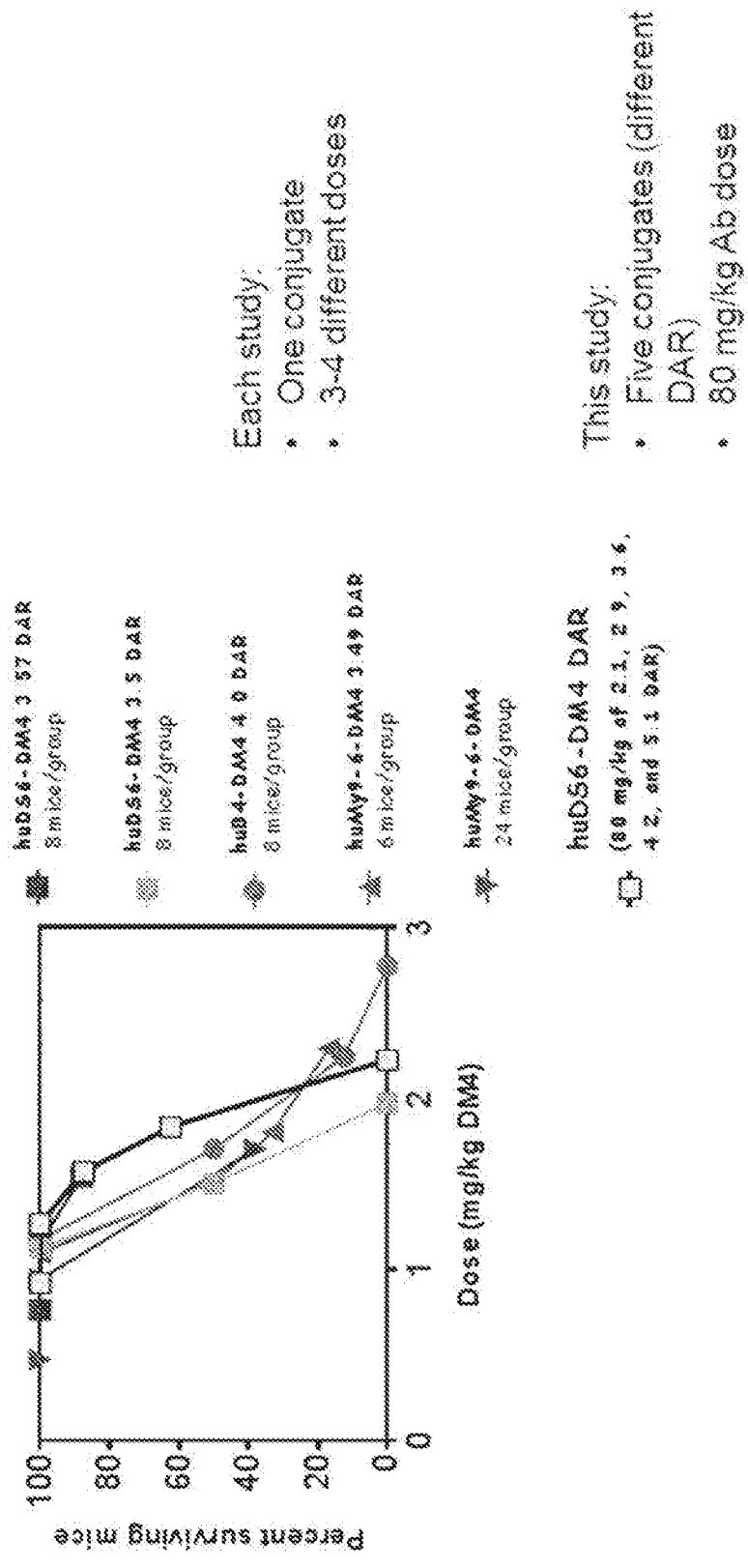
FIG. 8 is a graph showing in vivo toxicity studies in mice that received antibody-SPDB-DM4 conjugates of various DARs, including ADC huDS6-SPDB-DM4 ("huDS6-DM4"); huB4-SPDB-DM4 ("huB4-DM4"); and huMy9-6-SPDB-DM4 ("huMy9-6-DM4").

This in vivo analysis was extended to antibody-SPDB-DM4 conjugates, including huDS6-SPDB-DM4, huB4-SPDB-DM4, and huMy9-6-SPDB-DM4 (FIG. 8). The ADC huDS6-SPDB-DM4 (also known as "huDS6-DM4") is the humanized monoclonal antibody, huDS6, linked to DM4, a potent cytotoxic maytansinoid through a cleavable disulfide cross-linking agent N-Succinimidyl-4-2-pyridyldithio butanoate acid (SPDB). The ADC huDS6-SPDB-DM4 targets solid tumors such as ovarian, breast, cervical, lung and pancreatic carcinomas. The ADC huB4-SPDB-DM4 (also known as "huB4-DM4") is a novel antibody-drug conjugate that is composed of a humanized monoclonal IgG1 anti-CD19 antibody (huB4) attached to DM4 through a cleavable disulfide cross-linking agent N-Succinimidyl-4-2-pyridyldithio butanoate acid (SPDB). The ADC huMy9-6-SPDB-DM4 (also known as "huMy9-6-DM4") is an ADC that specifically binds CD33, a siglec family antigen expressed primarily on myeloid cells. The ADC huMy9-6-SPDB-DM4 has undergone clinical evaluation for the treatment of acute myeloid leukemia.

As shown in FIG. 8, the specified conjugate was administered at 3-4 different doses and mouse survival was measured as an indicator of toxicity. The DAR range for the 4 conjugates was narrow (ranging from 3.49 to 4.0); thus, the $LD_{50}$ range (the dose that is lethal to 50% of the animals) was also narrow (DM4 dose between 1.6-2 mg/kg). Conjugates having different DAR were administered at 80 mg/kg antibody dose, and mouse survival was measured as an indicator of toxicity (FIG. 8). The similar result for all conjugates, regardless of DAR, indicates that the toxicity is driven by the total DM4 dose administered. That is, within the DAR range of 2.1 to 5.1 the toxicity is not affected by different DAR.

Example 5: Formulating ADC Therapeutic Compositions Based on Drug Concentration Minimizes Potency Variations Resulting from DAR Variations Conventionally, antibody drug conjugate therapeutic compositions have been formulated based on antibody concentration. FIG. 9A shows the variability inherent in formulating antibody drug conjugates based on antibody concentration, even when remaining within the allowable ranges of the specification. In particular, at the end of the ADC manufacturing process, the concentration of antibody is measured, and the antibody is diluted to reach the target antibody concentration, which is 5.0 mg/ml for huMov19-sulfo-SPDB-DM4. In FIG. 9A, the target antibody concentration (5.0 mg/ml) is boxed and the target DAR (3.4) is circled for huMov19-sulfo-SPDB-DM4. At this target antibody concentration, the DM4 concentration is 91.1 µg/ml. In practice, the antibody concentration in the finished drug product is allowed to vary from the target concentration. The antibody concentration in the finished product could be as low as 4.0 mg/ml or as high as 6.0 mg/ml. Thus, as shown by the boxed area of DM4 concentrations, depending on the DAR, the DM4 concentration in the finished drug product could be as low as 62.1 µg/ml or as high as 125.4 µg/ml.

Formulating the ADC composition based on DM4 concentration and adding a DM4 concentration specification of +/−10% significantly narrows the potency present in the finished drug product to +/−10% of the target DM4 concentration (shown in highlight; +/−10% specification).

The liability for batches failing to conform to specification is shown at FIG. 9B where the target DM4 concentration and DAR are highlighted. DM4 concentration is shown at the top, DAR is shown at left, and the resulting antibody concentration is shown within the highlighted box (5.0 mg/ml). When the antibody concentration varies more than ±20% from the target, that batch is out of specification. The concentration of antibody present in batches failing to conform to specification is shown in bold (FIG. 9B). The risk of batches failing to conform to specification is fairly low.

In sum, the current formulation specification allows ±20% variation in antibody-based concentration (4.0-6.0 mg/mL). Thus, the ADC potency could vary by as much as ±35% depending on the DAR. By formulating the ADC based on DM4 concentration and allowing no more than ±10% variation in DM4 concentration, potency is permitted to vary by only ±10%. Thus, the new formulation method eliminates DAR potency dependence by formulating to a narrow range of DM4 concentration. Such a formulation strategy only slightly increases the risk of a batch failing to conform to specification due to the antibody concentration being outside its specification.

Example 6: DAR Conjugate Formulation

The ADC huMov19-sulfo-SPDB-DM4, which comprises an huMov19 antibody, SPDB linker and the cytotoxic drug, DM4, is an example of an ADC where the in vitro potency, in vivo efficacy, and in vivo toxicity are independent of DAR and are driven entirely by the administered concentration of DM4. Thus, huMov19-sulfo-SPDB-DM4 is a good candidate for formulating by DM4 rather than huMov19 concentration. In order to test the hypothesis that this would narrow the drug product potency a series of huMov19-sulfo-SPDB-DM4 conjugates having a range of DARs were manufactured. The conjugates were purified into base formulation buffer (10 mM sodium acetate, 9% (w/v) sucrose, pH 5.0) and the DM4 and huMov19 antibody concentration for each sample was measured spectrophotometrically at wavelengths 252 nm and 280 nm, respectively. The molar concentration of DM4 and huMov19 antibody comprising the $$C_{DM4}(M) = \frac{A_{252} - 0.348 A_{280}}{24177}$$

$$C_{Ab}(M) = \frac{A_{280} - (5323)C_{DM4}}{201400}$$

Each of the various DAR conjugates was formulated in two different ways: one was diluted with the base formulation buffer to reach the target huMov19 antibody concentrations within the specification range of 5.0 mg/mL ±20%. In addition, the various DAR conjugates were formulated to target DM4 concentrations within the proposed specification of 91.1 µg/mL ±10%. All samples were subjected to Specific Cytotoxicity assay.

The Specific Cytotoxicity assay involves incubating Folate Receptor 1 (FOLR1) positive cells (KB) in the presence of media containing a dilution series of huMov19-sulfo-SPDB-DM4 drug conjugate in duplicate wells of a sterile, 96-well, flat bottomed black tissue culture plate with clear bottom. Each assay plate contains a reference, control and a test article series of identical dilutions in wells with KB cells and media blanks. After a 4-day incubation period at 37° C.±2° C., the plates are removed from the incubator and allowed to equilibrate to room temperature for 1 hour prior to the addition of CellTiter-Glo™ Luminescent Cell Viability Reagent. The plates are incubated for an additional 2 hours prior to analyzing for and recording the luminescent signal on the Victor III plate reader. CellTiter-Glo™ uses a unique, stable form of luciferase to measure ATP as an indicator of viable cells. The luminescent signal produced is directly proportional to the number of viable cells present in the well and likewise inversely proportional to the cytotoxicity of the drug in that well. Because the luciferase reaction requires ATP, conditions have been created such that the amount of light produced is proportional to the amount of ATP present, reflecting the number of viable cells. The three plate data file is imported into PLA 2.0 software and the $EC_{50}$ values for reference and test article are determined from the constrained 4 parameter logistic curve fit using all 6 replicates for each sample. For samples passing acceptance criteria for slope difference and parallelism, the % relative potency of the test article is reported from the IC50s derived from the constrained 4PL curve fit. Percent potency is calculated as follows.

$$\% \text{ Potency} = \frac{EC_{50}(\text{reference standard})100\%}{EC_{50}(\text{test article})}$$

If the test article $EC_{50}$ is lower than the reference standard $EC_{50}$, this indicates that the test article has greater potency than the reference standard and the calculated % potency will be greater than 100%. Conversely, if the test article $EC_{50}$ is greater than the reference standard $EC_{50}$ this indicates that the test article has less potency than the reference standard and the calculated % potency will be less than 100%.

The results of these calculations are shown in Table 2 and Table 3 (below). The Reference Standard used for the Potency Assays in Table 2 was Sample A, whereas the Reference standard used for the Potency Assays in Table 3 was Sample F. The dilution series for each sample was made assuming a nominal concentration of 5 mg/mL huMov19 to mimic the way the ADC is dosed in a clinical setting. When huMov19-sulfo-SPDB-DM4 ADCs are formulated to target an huMov19 concentration of 5 mg/mL (Table 2) there is a wide range of potencies as expected: 59.8-124.6% for a total of ~2× difference between highest and lowest potency ADCs. This is in good agreement with the expected range of 35%. In contrast when huMov19-sulfo-SPDB-DM4 ADCs of various DARs are formulated to target a DM4 concentration of 91.0 mg/mL, the resulting relative potency range is much narrower: 80.9-106.5% for a total of ~1×. This is in good agreement with the expected range of 10%. Most measured potencies are within 15% of the expected value based on the DM4 concentration. This is within the combined experimental error of both the potency and concentration measurement assays. Taken together these results show the advantage of formulating to a DM4 concentration target rather than an huMov19 concentration target as is typical for ADCs.

TABLE 2 huMov19-sulfo-SPDB-DM4 conjugates manufactured at various DARs (±15% and formulated to target various huMov19 concentrations (±20%).

| | Manufacturing Target | | Measured Values (UV) | | | Expected | Measured | |
|---|---|---|---|---|---|---|---|---|
| Sample | DAR | [Ab] mg/mL | [Ab] mg/mL | [DM4] µg/mL | DAR | % Potency | % Potency | % Difference |
| A | 3.4 | 5.0 | 5.1 | 92.3 | 3.4 | 100.0 | 93.0 | −7.0 |
| B | 2.9 | 4.0 | 4.0 | 63.0 | 2.9 | 68.2 | 59.8 | −8.4 |
| C | 3.9 | 4.0 | 4.0 | 83.5 | 3.9 | 90.5 | 91.3 | 0.8 |

TABLE 2-continued huMov19-sulfo-SPDB-DM4 conjugates manufactured at various DARs (±15% and formulated to target various huMov19 concentrations (±20%).

| | Manufacturing Target | | Measured Values (UV) | | | Expected | Measured | |
|---|---|---|---|---|---|---|---|---|
| Sample | DAR | [Ab] mg/mL | [Ab] mg/mL | [DM4] µg/mL | DAR | % Potency | % Potency | % Difference |
| D | 2.9 | 6.0 | 5.9 | 93.5 | 2.9 | 101.4 | 93.2 | −8.2 |
| E | 3.9 | 6.0 | 6.0 | 126.3 | 3.9 | 136.9 | 124.6 | −12.3 |

TABLE 3 huMov19-sulfo-SPDB-DM4 conjugates manufactured at various DARs (15%) and formulated to target various DM4 concentrations (10%).

| | Manufacturing Target | | Measured Values (UV) | | | Expected | Measured | |
|---|---|---|---|---|---|---|---|---|
| Sample | DAR | [DM4] g/mL | [Ab] mg/mL | [DM4] µg/mL | DAR | % Potency | % Potency | % Difference |
| F | 3.4 | 91.0 | 5.2 | 94.1 | 3.4 | 100.0 | 92.2 | −7.8 |
| G | 2.9 | 82.0 | 5.6 | 87.3 | 2.9 | 92.8 | 86.0 | −6.8 |
| H | 3.4 | 82.0 | 4.6 | 84.2 | 3.4 | 89.5 | 86.2 | −3.3 |
| I | 3.9 | 84.0 | 4.2 | 87.3 | 3.9 | 92.8 | 84.3 | −8.5 |
| J | 2.9 | 91.0 | 6.1 | 95.9 | 2.9 | 102.0 | 80.9 | −21.1 |
| K | 3.9 | 91.0 | 4.6 | 95.8 | 3.9 | 101.9 | 102.1 | 0.2 |
| L | 2.9 | 92.0 | 6.2 | 97.1 | 2.9 | 103.3 | 92.4 | −10.9 |
| M | 3.4 | 100.0 | 5.8 | 105.4 | 3.4 | 112.1 | 106.5 | −5.6 |
| N | 3.9 | 100.0 | 4.9 | 103.5 | 3.9 | 110.0 | 106.1 | −3.9 |

Example 7: Targeting Variable Antibody and Drug Concentration Tightens the Specification Window Over a Broader DAR Range In some instances, it may be desirable to allow variation in the targeted drug concentration to arrive at smaller variations for both drug and antibody concentrations rather than large variations in the non-targeted concentration (e.g., the antibody concentration). Formulating an ADC composition using such method maximizes specification range by targeting the middle of the range where both the antibody and drug concentration overlap at a particular DAR value. In practice, drug specifications are tighter than the antibody specifications (e.g. ±10% for drug versus ±15% for the antibody). Thus, allowing smaller variations in antibody and drug concentrations provide an additional control strategy to achieve tighter drug concentration specification (rather than an absolute target) while minimizing risk of batches that, although not conforming to specification, would be perfectly safe to use.

The desirability of formulating an ADC using the method described above is shown for huMy9-6-sulfo-SPDB-DGN462, which is a CD33-targeted antibody drug conjugate comprising the antibody huMy9-6, conjugated to a novel DNA-alkylating agent, DGN462 via a cleavable disulfide linker, sulfo-SPDB.

Figure 10B:
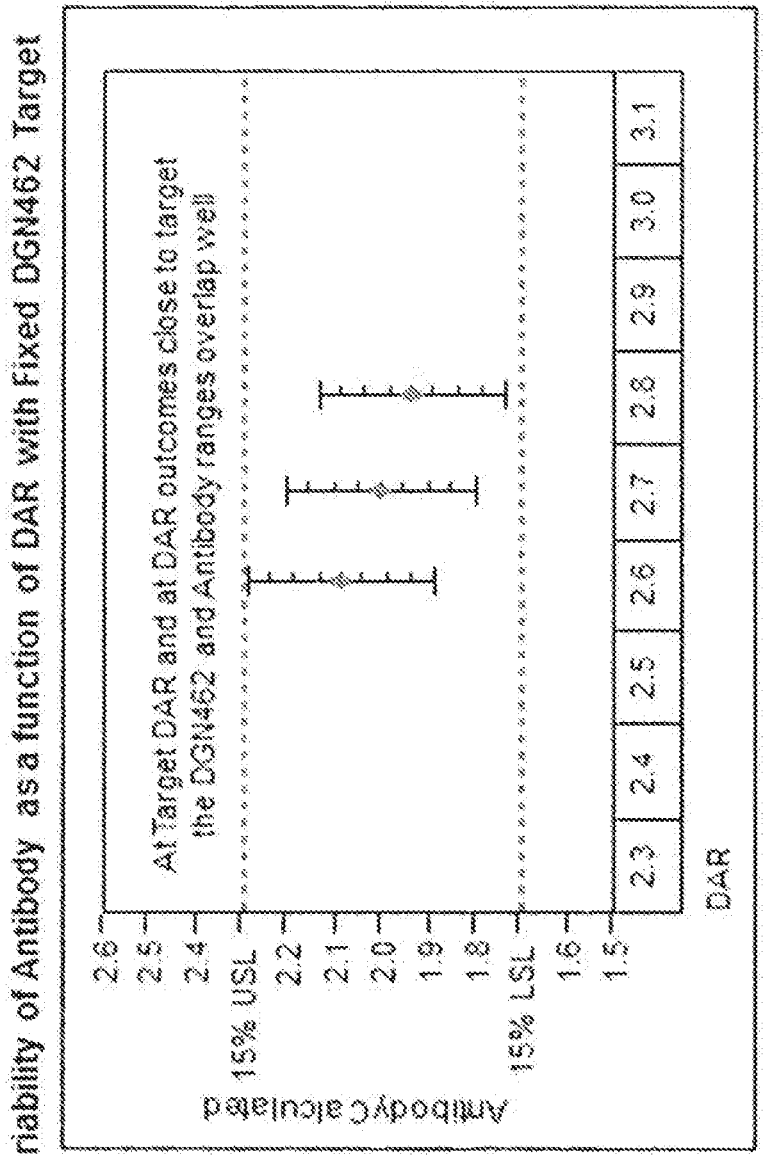
Figure 10C:
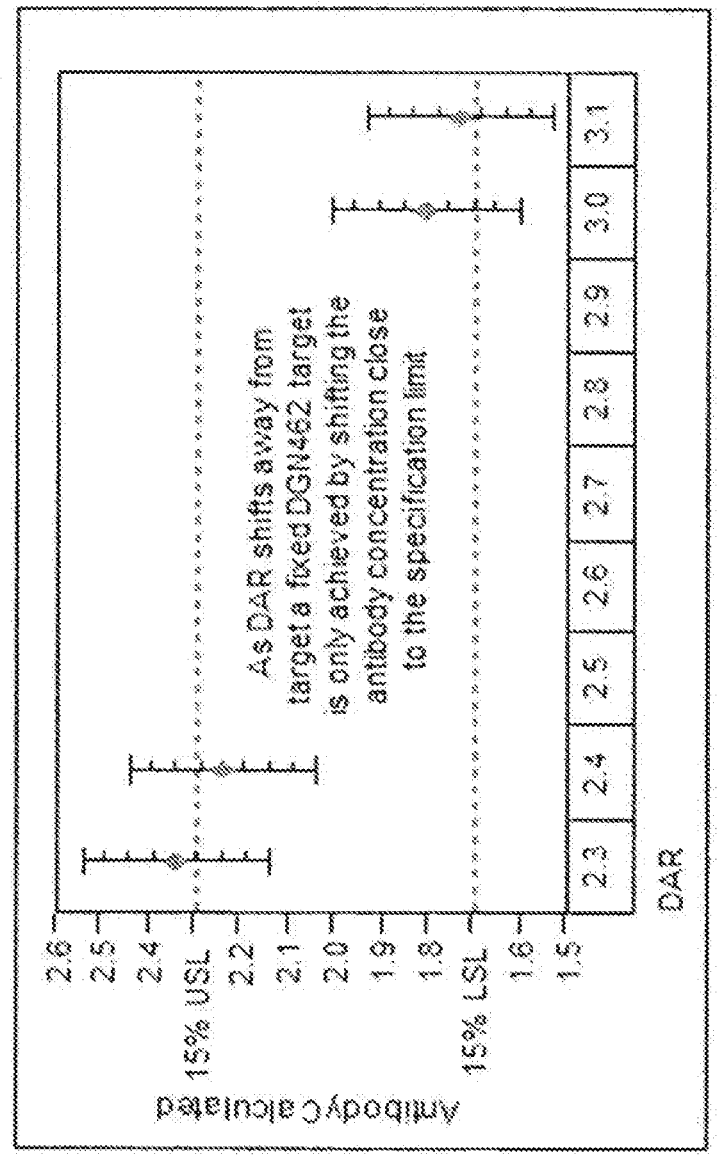
Figure 11A:
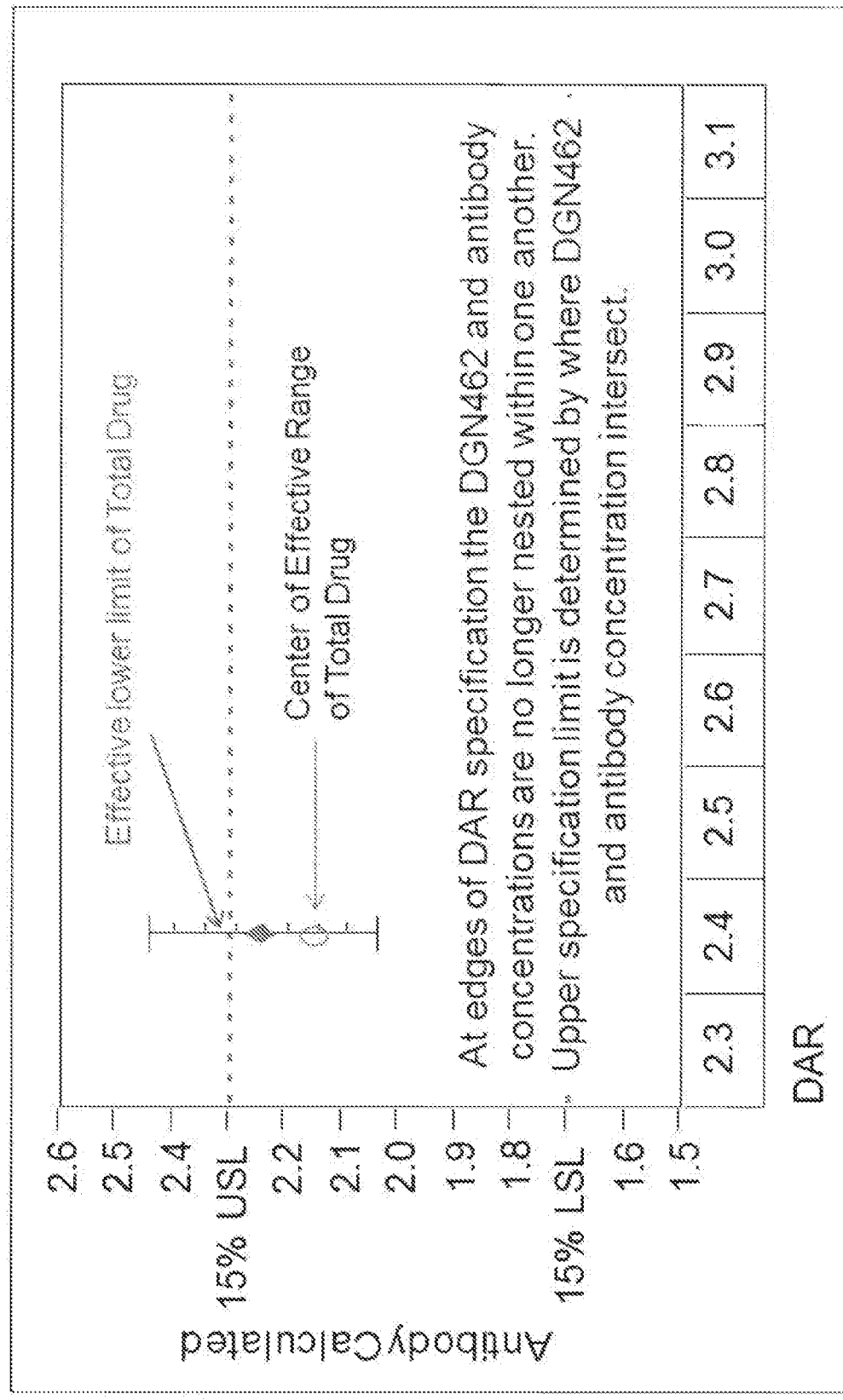
FIGS. 11A-11C are graphs showing that formulating an ADC composition by varying antibody and drug concentration (open ovals) narrows the permitted specification range for both the antibody and the drug relative to varying only antibody specification to achieve a target drug concentration (gray diamonds).

In each of FIGS. 10A, 10B, and 10C, the upper and lower limit of the antibody specification range is indicated by a dashed line, the X axis indicates the DAR of a batch of drug, where the target DAR is 2.7; the vertical lines show the upper and lower DGN462 specification limits at a given DAR, and the dark gray diamond on each vertical line indicates the overlap between the DGN462 specification range and the antibody specification range at a particular DAR. In FIG. 11A, when DAR for the batch is 2.7, the center of the DGN462 specification range falls squarely within the center of the antibody range. In FIG. 10B, when DAR for the batch is close to the target DAR, the antibody concentration needed to achieve a fixed DGN462 target concentration falls well within the upper and lower specification limits for antibody. In FIG. 10C, when the DAR for a batch approaches the upper and lower DAR specification limits, 3.0-3.1 and 2.3-2.4, respectively, the fixed DGN462 concentration lies close to or beyond the defined antibody concentration specification because the amount of antibody needed to achieve the DGN462 target concentration approaches the upper and lower specification limits for antibody concentration. Improved formulation methods are therefore desirable.

Figure 11B:
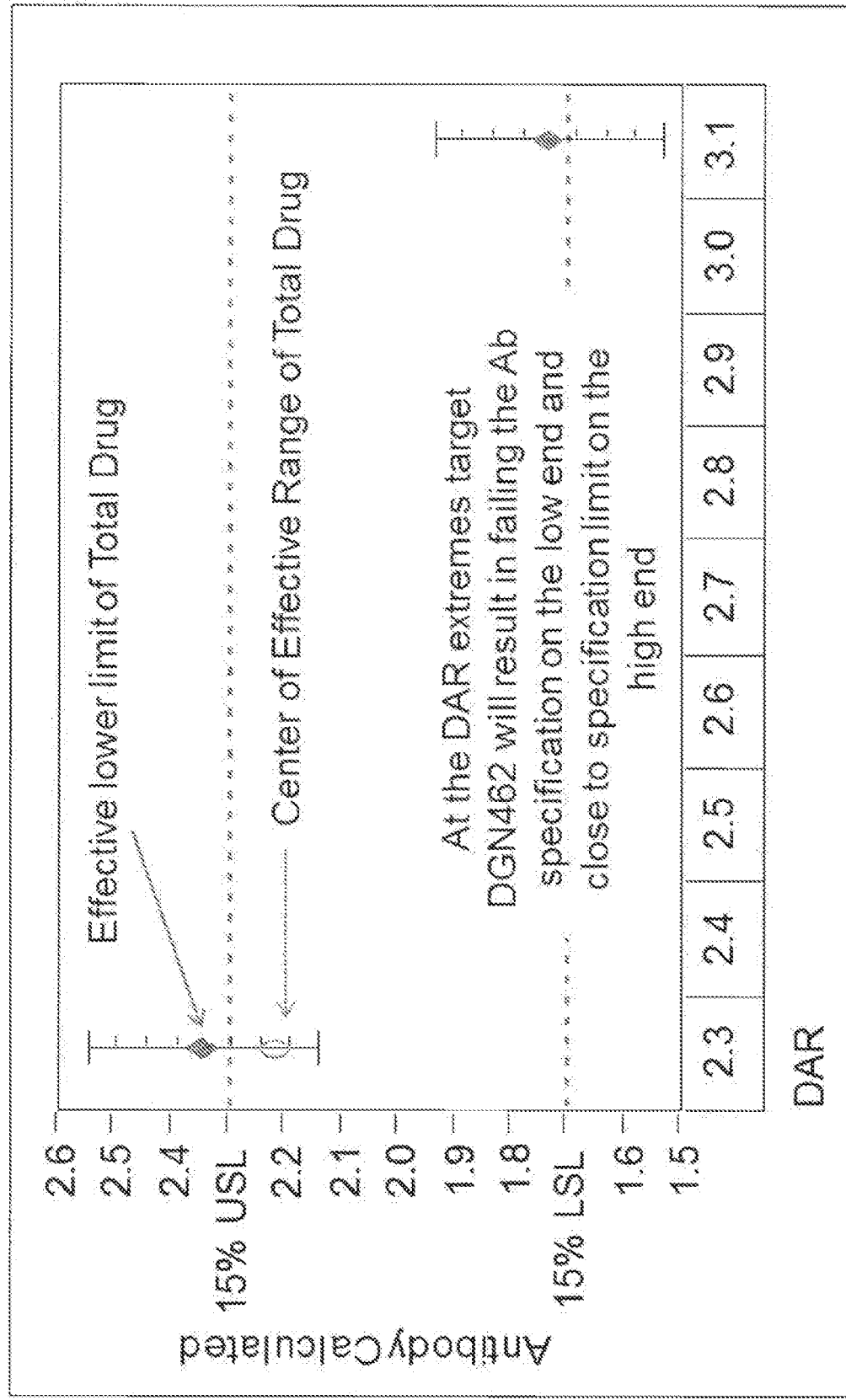
Figure 11C:
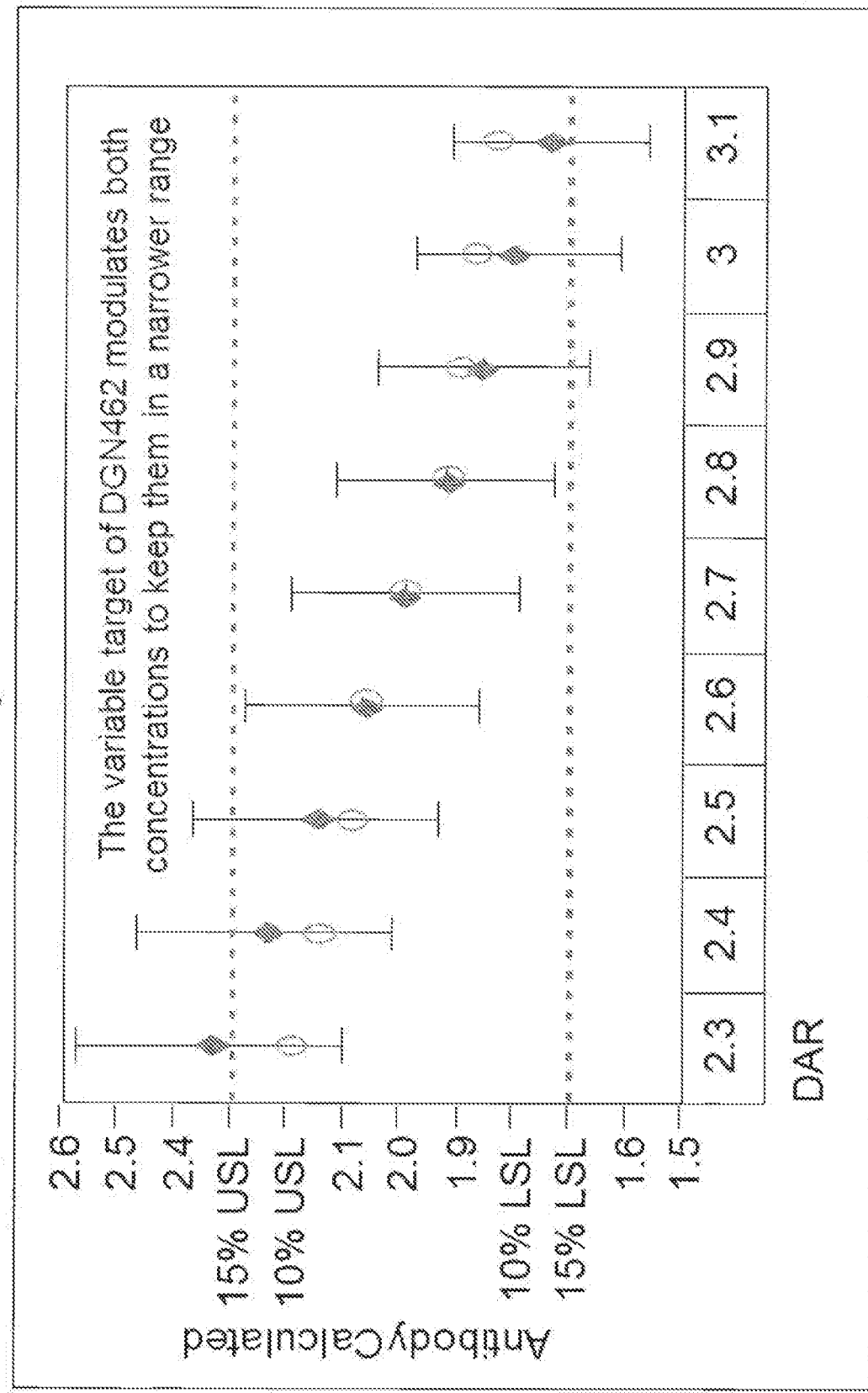

FIGS. 11A-11C show the improvement to be gained by allowing both DGN462 and antibody concentration to vary—particularly when the DAR approaches the upper and lower DAR specification limits (e.g., 3.0-3.1 and 2.3-2.4). Targeting a variable drug concentration identifies the middle of the range where the antibody concentration specification range and the drug concentration specification range overlap (FIG. 11A). The center of the effective range of total drug is well below the antibody upper specification limit. Thus, at upper and lower DAR specification limits, the method of targeting a variable DGN462 limits the target antibody concentration to vary +/−10% from target instead of the full ±15% generating a more consistent product. In contrast, for batches where the DAR approaches the upper and lower limits, varying antibody concentration to achieve a fixed DGN462 target concentration causes larger deviations from target antibody concentration and increases the risk of potency and toxicity variability (FIGS. 11A and 11B). FIG. 11C illustrates the improvement provided by the method of targeting a variable drug concentration at the upper and lower DAR specification limits, where the DGN462 concentration and the antibody concentration are maintained between narrower limits of 4% (open ovals) compared to where the antibody concentration is used to achieve a target drug concentration (gray diamonds), in which the fixed target total drug exceeds the upper specification limit for antibody at a DAR of 2.3.

The following equations are useful for calculating upper specification limits and lower specification limits for a drug.

$$USL(\text{drug}) \, \mu g/mL = \frac{\text{Upper Antibody Concentration Specification Limit} \times DAR \times \text{Drug Mol. Wt.}}{\text{Antibody Mol. Wt.}} \times 1000$$

$$LSL(\text{drug}) \, \mu g/mL = \frac{\text{Lower Antibody Concentration Specification Limit} \times DAR \times \text{Drug Mol. Wt.}}{\text{Antibody Mol. Wt.}} \times 1000$$

Table 4 illustrates methods used to calculate the upper and lower specification limit of DGN462 (USL DGN462, LSL DGN462). Upper Antibody Concentration Specification Limit is constant. DAR is empirically determined for a batch of antibody drug conjugate. The calculations according to the desired upper and lower specification limits were performed as follows:

$$USL(DGN462) = \frac{2.30 \times DAR \times 1024}{146192} \times 1000 \, \mu g/mL$$

$$LSL(DGN462) = \frac{1.70 \times DAR \times 1024}{146192} \times 1000 \, \mu g/mL$$

The values "2.30" and "1.70" define the upper and lower antibody specification limits. The denominator is the molecular weight of the antibody.

TABLE 4

Calculated DGN462 Concentrations based on Antibody Specification Limits

| | Target | | | | | | | | |
|---|---|---|---|---|---|---|---|---|---|
| DAR | 2.3 | 2.4 | 2.5 | 2.6 | 2.7 | 2.8 | 2.9 | 3 | 3.1 |
| DGN462 LSL | 27.4 | 28.6 | 29.8 | 31.0 | 32.2 | 33.3 | 34.5 | 35.7 | 36.9 |
| DGN462 USL | 35.4 | 37.0 | 38.5 | 40.1 | 41.6 | 43.1 | 44.7 | 46.2 | 47.8 |
| Ab Concentration based on static DGN462 concentration | 2.3 | 2.3 | 2.2 | 2.1 | 2.0 | 1.9 | 1.9 | 1.8 | 1.7 |
| Formulating by DGN462 (Based on variable target) | | | | | | | | | |
| DAR | 2.3 | 2.4 | 2.5 | 2.6 | 2.7 | 2.8 | 2.9 | 3 | 3.1 |
| DGN462 LSL | 34.0 | 34.0 | 34.0 | 34.0 | 34.0 | 34.0 | 34.5 | 35.7 | 36.9 |
| DGN462 USL | 35.4 | 37.0 | 38.5 | 40.1 | 41.6 | 41.6 | 41.6 | 41.6 | 41.6 |
| D6N462 Target | 34.7 | 35.5 | 36.3 | 37.1 | 37.8 | 37.8 | 38.1 | 38.7 | 39.3 |
| Range around Target | 2% | 4% | 6% | 8% | 10% | 10% | 9% | 8% | 6% |
| Resulting Antibody Range | | | | | | | | | |
| huMy9-6 LSL | 2.1 | 2.0 | 1.9 | 1.9 | 1.8 | 1.7 | 1.7 | 1.7 | 1.7 |
| huMy9-6 USL | 2.2 | 2.2 | 2.2 | 2.2 | 2.2 | 2.1 | 2.0 | 2.0 | 1.9 |
| Variable DGN462 concentration | 2.2 | 2.1 | 2.1 | 2.0 | 2.0 | 1.9 | 1.9 | 1.8 | 1.8 |

When calculating LSL and USL at certain points these limits will fall outside of the proposed specification
These outliers can be set to either the LSL (34.0 mg/mL) or the USL (41.5 mg/mL) using a > or < rule
Proposal is to report DAR to second decimal place for formulation purposes In the following example, an ADC is formulated by targeting variable drug concentration. Here the ADC includes a non-functional antibody, huMov19 (MW of 145676 g/mol) conjugated to D2 (MW 961.05 g/mol) with a target DAR of 2.7, antibody concentration of 2.0 mg/mL, and cytotoxic agent concentration of 39.2 µg/mL. The ADC is formulated to target a variable concentration of drug to minimize the offset from target for the antibody concentration. As shown in FIG. 11A, targeting a variable drug concentration varies the resulting antibody concentration by ±10% (1.8-2.2) versus ±15% when a static drug concentration is utilized (FIG. 11A; see, e.g., Tables 4-7). Targeting a variable drug identifies the middle of the range where the antibody specification range and the drug specification range overlap (FIG. 11A; see, e.g., Tables 4-7).

Table 5 below illustrates methods used to calculate the upper and lower specification limit of D2 (USL D2, LSL D2). The Upper and Lower Antibody Concentration Specification Limits are constant and the DAR is empirically determined.

TABLE 5

Calculated D2 Concentrations based on Antibody Specification Limits

| | Target | | | | | | | | |
|---|---|---|---|---|---|---|---|---|---|
| DAR | 2.3 | 2.4 | 2.5 | 2.6 | 2.7 | 2.8 | 2.9 | 3 | 3.1 |
| D2 LSL | 25.8 | 26.9 | 28.0 | 29.2 | 30.3 | 31.4 | 32.5 | 33.6 | 34.8 |
| D2 USL | 33.4 | 34.8 | 36.3 | 37.7 | 39.2 | 40.6 | 42.1 | 43.5 | 45.0 |
| Ab Concentration based on static D2 concentration | 2.3 | 2.3 | 2.2 | 2.1 | 2.0 | 1.9 | 1.9 | 1.8 | 1.7 |
| Formulating by D2 (Based on variable target) | | | | | | | | | |
| DAR | 2.3 | 2.4 | 2.5 | 2.6 | 2.7 | 2.8 | 2.9 | 3 | 3.1 |
| D2 LSL | 32.1 | 32.1 | 32.1 | 32.1 | 32.1 | 32.1 | 32.5 | 33.6 | 34.8 |
| D2 USL | 33.4 | 34.8 | 36.3 | 37.7 | 39.2 | 39.2 | 39.2 | 39.2 | 39.2 |
| D2 Target | 32.7 | 33.4 | 34.2 | 34.9 | 35.6 | 35.6 | 35.9 | 36.4 | 37.0 |
| Range around Target | 2% | 4% | 6% | 8% | 10% | 10% | 9% | 8% | 6% |
| Resulting Antibody Range | | | | | | | | | |
| huMOV19 LSL | 2.1 | 2.0 | 1.9 | 1.9 | 1.8 | 1.7 | 1.7 | 1.7 | 1.7 |
| huMOV19 USL | 2.2 | 2.2 | 2.2 | 2.2 | 2.2 | 2.1 | 2.0 | 2.0 | 1.9 |
| Ab Concentration based on variable D2 concentration | 2.2 | 2.1 | 2.1 | 2.0 | 2.0 | 1.9 | 1.9 | 1.8 | 1.8 |

In another example, an ADC is formulated by targeting variable cytotoxic agent concentration. Here the ADC includes a functional antibody, huEGFR-7R (MW of 144975 g/mol) conjugated to D1 (MW 838 g/mol) with a target DAR of 2.7, antibody concentration of 2.0 mg/mL, and cytotoxic agent concentration of 34.3 µg/mL. The ADC is formulated to target a variable concentration of cytotoxic agent to minimize the offset from target for the antibody concentration.

Table 6 below illustrates methods used to calculate the upper and lower specification limit of D1 (USL D1, LSL D1). The Upper and Lower Antibody Concentration Specification Limits are constant and the DAR is empirically determined.

TABLE 6

Calculated D1 Concentrations based on Antibody Specification Limits

| | Target | | | | | | | | |
|---|---|---|---|---|---|---|---|---|---|
| DAR | 2.3 | 2.4 | 2.5 | 2.6 | 2.7 | 2.8 | 2.9 | 3 | 3.1 |
| D1 LSL | 22.6 | 23.6 | 24.6 | 25.5 | 26.5 | 27.5 | 28.5 | 29.5 | 30.5 |
| D1 USL | 29.2 | 30.5 | 31.8 | 33.1 | 34.3 | 35.6 | 36.9 | 38.2 | 39.4 |
| Ab Concentration based on static D1 concentration | 2.3 | 2.3 | 2.2 | 2.1 | 2.0 | 1.9 | 1.9 | 1.8 | 1.7 |
| Formulating by D1 (Based on variable target) | | | | | | | | | |
| DAR | 2.3 | 2.4 | 2.5 | 2.6 | 2.7 | 2.8 | 2.9 | 3 | 3.1 |
| D1 LSL | 28.1 | 28.1 | 28.1 | 28.1 | 28.1 | 28.1 | 28.5 | 29.5 | 30.5 |
| D1 USL | 29.2 | 30.5 | 31.8 | 33.1 | 34.3 | 34.3 | 34.3 | 34.3 | 34.3 |
| D1 Target | 28.7 | 29.3 | 29.9 | 30.6 | 31.2 | 31.2 | 31.4 | 31.9 | 32.4 |
| Range around Target | 2% | 4% | 6% | 8% | 10% | 10% | 9% | 8% | 6% |
| Resulting Antibody Range | | | | | | | | | |
| huEGFR-7R LSL | 2.1 | 2.0 | 1.9 | 1.9 | 1.8 | 1.7 | 1.7 | 1.7 | 1.7 |
| huEGFR-7R USL | 2.2 | 2.2 | 2.2 | 2.2 | 2.2 | 2.1 | 2.0 | 2.0 | 1.9 |
| Ab Concentration based on variable D1 concentration | 2.2 | 2.1 | 2.1 | 2.0 | 2.0 | 1.9 | 1.9 | 1.8 | 1.8 |

In yet another example, an ADC is formulated by targeting variable cytotoxic agent concentration. Here the ADC includes a functional antibody, huMy9-6 (MW of 146192 g/mol) conjugated to D10 (MW 1062.22 g/mol) with a target DAR of 2.7, antibody concentration of 2.0 mg/mL, and cytotoxic agent concentration of 44.0 μg/mL. The ADC is formulated to target a variable concentration of cytotoxic agent to minimize the offset from target for the antibody concentration.

Table 7 below illustrates methods used to calculate the upper and lower specification limit of D1 (USL D1, LSL D1). The Upper and Lower Antibody Concentration Specification limits are constant and the DAR is empirically determined.

TABLE 7

Calculated D10 Concentrations based on Antibody Specification Limits

| | Target | | | | | | | | |
|---|---|---|---|---|---|---|---|---|---|
| DAR | 2.3 | 2.4 | 2.5 | 2.6 | 2.7 | 2.8 | 2.9 | 3 | 3.1 |
| D10 LSL | 28.4 | 29.6 | 30.9 | 32.1 | 33.4 | 34.6 | 35.8 | 37.1 | 38.3 |
| D10 USL | 36.8 | 38.4 | 40.0 | 41.6 | 43.2 | 44.8 | 46.4 | 48.0 | 49.6 |
| Ab Concentration based on static D10 concentration | 2.3 | 2.3 | 2.2 | 2.1 | 2.0 | 1.9 | 1.9 | 1.8 | 1.7 |
| Formulating by D10 (Based on variable target) | | | | | | | | | |
| DAR | 2.3 | 2.4 | 2.5 | 2.6 | 2.7 | 2.8 | 2.9 | 3 | 3.1 |
| D10 LSL | 35.3 | 35.3 | 35.3 | 35.3 | 35.3 | 35.3 | 35.8 | 37.1 | 38.3 |
| D10 USL | 36.8 | 38.4 | 40.0 | 41.6 | 43.2 | 43.2 | 43.2 | 43.2 | 43.2 |
| D10 Target | 36.0 | 36.8 | 37.6 | 38.4 | 39.2 | 39.2 | 39.5 | 40.1 | 40.7 |
| Range around Target | 2% | 4% | 6% | 8% | 10% | 10% | 9% | 8% | 6% |
| Resulting Antibody Range | | | | | | | | | |
| huMy9-6 LSL | 2.1 | 2.0 | 1.9 | 1.9 | 1.8 | 1.7 | 1.7 | 1.7 | 1.7 |
| huMy9-6 USL | 2.2 | 2.2 | 2.2 | 2.2 | 2.2 | 2.1 | 2.0 | 2.0 | 1.9 |
| Ab Concentration based on variable D10 concentration | 2.2 | 2.1 | 2.1 | 2.0 | 2.0 | 1.9 | 1.9 | 1.8 | 1.8 |

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of reducing potency variability in a composition comprising a huMy9-6-sulfo-SPDB-DGN462 antibody benzodiazepine conjugate, the method comprising:
   (a) measuring the drug-to-antibody ratio (DAR) for the antibody drug conjugate composition;
   (b) determining the upper antibody specification limit and the lower antibody specification limit, wherein the upper antibody specification limit is the target antibody concentration plus the maximum variation allowed by the specification and the lower antibody specification limit is the target antibody concentration minus the maximum variation allowed by the specification;
   (c) determining the defined upper benzodiazepine specification limit and the defined lower benzodiazepine specification limit, wherein the defined upper benzodiazepine specification limit is the target benzodiazepine concentration plus the maximum variation allowed by the specification and the defined lower benzodiazepine specification limit is the target benzodiazepine concentration minus the maximum variation allowed by the specification;
   (d) determining the calculated upper benzodiazepine specification limit (USL (drug)) as follows:

$$USL(\text{drug})\,\mu g/mL = \frac{\text{Upper Antibody Concentration Specification Limit} \times DAR \times \text{Drug Mol. Wt.}}{\text{Antibody Mol. Wt.}} \times 1000$$

(e) determining the calculated lower benzodiazepine specification limit (LSL (drug)) as follows:

$$LSL(\text{drug})\,\mu g/mL = \frac{\text{Lower Antibody Concentration Specification Limit} \times DAR \times \text{Drug Mol. Wt.}}{\text{Antibody Mol. Wt.}} \times 1000$$

(f) comparing the calculated USL (drug) of step (d) to the defined upper benzodiazepine specification limit of step (c), and selecting the lower of the two values as the effective upper benzodiazepine specification limit;
   (g) comparing the calculated LSL (drug) of step (e) to the defined lower benzodiazepine specification limit of step (c), and selecting the higher of the two values as the effective lower benzodiazepine specification limit; and
   (h) formulating the antibody benzodiazepine conjugate composition to a target benzodiazepine concentration that is the midpoint between the effective upper benzodiazepine specification limit and the effective lower benzodiazepine specification limit, thereby reducing potency variability in said composition.

2. The method of claim 1, wherein the method narrows the range of the upper and lower specification limits for the drug and the antibody to about ±3-5%.

3. The method of claim 1, wherein the method narrows the range of the upper and lower specification limits to about ±4%.

4. The method of claim 1, wherein the maximum variation allowed by the specification in step (b) is about ±15%.

5. The method of claim 1, wherein the maximum variation allowed by the specification in step (b) is less than about ±10, 11, 12, 13, or 14%.

6. The method of claim 1, wherein the maximum variation allowed by the specification in step (c) is about ±15%.

7. The method of claim 1, wherein the maximum variation allowed by the specification in step (c) is less than about ±10, 11, 12, 13, or 14%.

\* \* \* \* \*

SEQUENCE LISTING

```
<160> NUMBER OF SEQ ID NOS: 17

<210> SEQ ID NO 1
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Ile Val Leu Thr Gln Ser Pro Ala Ile Met Ser Ala Ser Pro Gly
1               5                   10                  15

Glu Arg Val Thr Met Thr Cys Ser Ala Ser Ser Gly Val Asn Tyr Met
            20                  25                  30

His Trp Tyr Gln Gln Lys Pro Gly Thr Ser Pro Arg Arg Trp Ile Tyr
        35                  40                  45
```

```
Asp Thr Ser Lys Leu Ala Ser Gly Val Pro Ala Arg Phe Ser Gly Ser
 50                  55                  60

Gly Ser Gly Thr Asp Tyr Ser Leu Thr Ile Ser Ser Met Glu Pro Glu
 65                  70                  75                  80

Asp Ala Ala Thr Tyr Tyr Cys His Gln Arg Gly Ser Tyr Thr Phe Gly
                 85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
        210

<210> SEQ ID NO 2
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Val Gln Pro Gly Ala Glu Val Val Lys Pro Gly Ala
 1               5                  10                  15

Ser Val Lys Leu Ser Cys Lys Thr Ser Gly Tyr Thr Phe Thr Ser Asn
            20                  25                  30

Trp Met His Trp Val Lys Gln Ala Pro Gly Gln Gly Leu Glu Trp Ile
        35                  40                  45

Gly Glu Ile Asp Pro Ser Asp Ser Tyr Thr Asn Tyr Asn Gln Asn Phe
 50                  55                  60

Gln Gly Lys Ala Lys Leu Thr Val Asp Lys Ser Thr Ser Thr Ala Tyr
 65                  70                  75                  80

Met Glu Val Ser Ser Leu Arg Ser Asp Thr Ala Val Tyr Tyr Cys
                 85                  90                  95

Ala Arg Gly Ser Asn Pro Tyr Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
            195                 200                 205

Pro Ser Asn Thr Lys Val Asp Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 3
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
```

```
                    85                  90                  95
Glu Tyr Pro Tyr Thr Phe Gly Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 4
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 5
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 6
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Ile Val Leu Thr Gln Ser Pro Ala Thr Met Ser Ala Ser Pro Gly
1               5                   10                  15

Glu Arg Val Thr Ile Thr Cys Ser Ala His Ser Ser Val Ser Phe Met
            20                  25                  30

His Trp Phe Gln Gln Lys Pro Gly Thr Ser Pro Lys Leu Trp Ile Tyr
        35                  40                  45

Ser Thr Ser Ser Leu Ala Ser Gly Val Pro Ala Arg Phe Gly Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Arg Ser Ser Phe Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 7
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Gln Ala Gln Leu Val Gln Ser Gly Ala Glu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
            35                  40                  45

Gly Tyr Ile Tyr Pro Gly Asn Gly Ala Thr Asn Tyr Asn Gln Lys Phe
        50                  55                  60

Gln Gly Lys Ala Thr Leu Thr Ala Asp Thr Ser Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg Gly Asp Ser Val Pro Phe Ala Tyr Trp Gly Gln Gly Thr Leu
                100                 105                 110

Val Thr Val Ser Ala Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415
```

```
Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
        435                 440                 445

<210> SEQ ID NO 8
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 9
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45
```

Gly Val Ile Tyr Pro Gly Asn Asp Ile Ser Tyr Asn Gln Lys Phe
 50                  55                  60

Gln Gly Lys Ala Thr Leu Thr Ala Asp Lys Ser Ser Thr Thr Ala Tyr
 65                  70                  75                  80

Met Gln Leu Ser Ser Leu Thr Ser Glu Asp Ser Ala Val Tyr Tyr Cys
                 85                  90                  95

Ala Arg Glu Val Arg Leu Arg Tyr Phe Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 10
<211> LENGTH: 214
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Tyr Gln His Lys Pro Gly Lys Gly Pro Lys Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Ser Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Asn Tyr
            20                  25                  30

Leu Ala Trp Tyr Gln His Lys Pro Gly Lys Gly Pro Lys Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Ser Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys Arg Thr Val Ala Ala

```
            100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 12
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Thr Ile Tyr Pro Gly Asp Gly Asp Thr Thr Tyr Thr Gln Lys Phe
    50                  55                  60

Gln Gly Lys Ala Thr Leu Thr Ala Asp Lys Ser Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 13
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
            20                  25                  30

Leu Ala Trp Tyr Gln Gln Lys Pro Gly Lys Ser Pro Lys Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Tyr Trp Gly Thr Thr Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 14
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Pro Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu

```
                    290                 295                 300
Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 15
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
                20                  25                  30

Gly Val Ser Trp Val Arg Gln Pro Pro Gly Lys Gly Leu Glu Trp Leu
            35                  40                  45

Gly Val Ile Trp Gly Asp Gly Ser Thr Asn Tyr His Ser Ser Leu Lys
        50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205
```

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 16
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Lys Arg Trp Ile Tyr
        35                  40                  45

Asp Thr Ser Asn Leu Pro Tyr Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 17
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly
                20                  25                  30

Phe Ala Trp His Trp Ile Arg Gln His Pro Gly Asn Lys Leu Glu Trp
            35                  40                  45

Met Gly Tyr Ile Leu Tyr Ser Gly Ser Thr Val Tyr Ser Pro Ser Leu
        50                  55                  60

Lys Ser Arg Ile Ser Ile Thr Arg Asp Thr Ser Lys Asn His Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu

-continued

```
                    260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly
```